United States Patent
Compans et al.

(10) Patent No.: US 9,683,020 B2
(45) Date of Patent: Jun. 20, 2017

(54) VLPS CONTAINING LIGANDS AND METHODS RELATED THERETO

(75) Inventors: Richard W. Compans, Atlanta, GA (US); Baozhong Wang, Duluth, GA (US); Fu Shi Quan, Gyeonggi-do (KR)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 22 days.

(21) Appl. No.: 14/236,618

(22) PCT Filed: Jul. 31, 2012

(86) PCT No.: PCT/US2012/049008
§ 371 (c)(1),
(2), (4) Date: May 5, 2014

(87) PCT Pub. No.: WO2013/019800
PCT Pub. Date: Feb. 7, 2013

(65) Prior Publication Data
US 2014/0255441 A1    Sep. 11, 2014

Related U.S. Application Data

(60) Provisional application No. 61/513,695, filed on Aug. 1, 2011, provisional application No. 61/527,636, filed on Aug. 26, 2011.

(51) Int. Cl.
| | |
|---|---|
| A61K 39/12 | (2006.01) |
| A61K 39/145 | (2006.01) |
| C07K 14/005 | (2006.01) |
| C07K 14/195 | (2006.01) |
| C12N 7/00 | (2006.01) |
| A61K 39/00 | (2006.01) |

(52) U.S. Cl.
CPC ........... *C07K 14/005* (2013.01); *A61K 39/12* (2013.01); *C07K 14/195* (2013.01); *C12N 7/00* (2013.01); *A61K 2039/5258* (2013.01); *A61K 2039/55516* (2013.01); *A61K 2039/64* (2013.01); *C07K 2319/02* (2013.01); *C07K 2319/03* (2013.01); *C12N 2710/14043* (2013.01); *C12N 2760/16122* (2013.01); *C12N 2760/16123* (2013.01); *C12N 2760/16134* (2013.01); *C12N 2760/18523* (2013.01); *C12N 2760/18534* (2013.01)

(58) Field of Classification Search
None
See application file for complete search history.

(56) References Cited

U.S. PATENT DOCUMENTS

| 7,763,450 B2 | 7/2010 | Robinson | |
|---|---|---|---|
| 9,045,727 B2 * | 6/2015 | Compans | ............... A61K 39/12 |
| 2006/0088909 A1 * | 4/2006 | Compans | ............. C07K 14/005 |
| | | | 435/69.1 |
| 2009/0162400 A1 * | 6/2009 | Powell | .................... A61K 39/12 |
| | | | 424/210.1 |
| 2010/0047277 A1 | 2/2010 | Compans | |
| 2010/0196419 A1 | 8/2010 | Compans | |
| 2010/0330190 A1 | 12/2010 | Compans | |
| 2011/0097358 A1 | 4/2011 | Galarza | |
| 2012/0052082 A1 | 3/2012 | Compans | |

FOREIGN PATENT DOCUMENTS

| WO | 2009079564 | 6/2009 | |
|---|---|---|---|
| WO | WO 2009079564 A2 * | 6/2009 | ............. C07K 19/00 |
| WO | 2010012069 | 2/2010 | |

OTHER PUBLICATIONS

Huleatt et al. "Potent immunogenicity and efficacy of a universal influenza vaccine candidate comprising a ecombinant fusion protein linking influenza M2e to the TLR5 ligand flagellin" Vaccine, 2008; 26: 201-214.

Moore et al. "A Chimeric A2 Strain of Respiratory Syncytial Virus (RSV) with the Fusion Protein of RSV Strain Line 19 Exhibits Enhanced Viral Load, Mucus, and Airway Dysfunction" Journal of Virology, 2009; 83: 4185-4194.

Olson et al. "Pulmonary immunity and immunopathology: lessons from respiratory syncytial virus" Expert Review of Vaccines, 2008; 7(8): 1239-1255.

Quan et al. "Viruslike Particle Vaccine Induces Protection Against Respiratory Syncytial Virus Infection in Mice" The Journal of Infectious Diseases, 2011; 204: 987-995.

Smith et al. "Toll-like receptor 5 recognizes a conserved site on flagellin required for protofilament formation and bacterial motility" Nature Immunology, 2003; 4(12): 1247-1253.

Song et al. "Vaccination inducing broad and improved cross protection against multiple subtypes of influenza A virus" PNAS, 2011; 108(2): 757-761.

Treanor et al. "Passively Transferred Monoclonal Antibody to the M2 Protein Inhibits Influenza A Virus Replication in Mice" Journal of Virology, 1990; 1375-1377.

Wang et al. "Incorporation of Membrane-Anchored Flagellin into Influenza Virus-Like Particles Enhances the Breadth of Immune Responses" Journal of Virology, 2008; 11813-11823.

Wang et al. "Enhanced Influenza Virus-Like Particle Vaccines Containing the Extracellular Domain of Matrix Protein 2 and a Toll-Like Receptor Ligand" Clinical and Vaccine Immunology, 2012; 19: 1119-1125.

Extended European Search Report for EP application No. 12820295.9 dated Feb. 3, 2015.

* cited by examiner

*Primary Examiner* — Agnieszka Boesen
(74) *Attorney, Agent, or Firm* — Emory Patent Group

(57) ABSTRACT

This disclosure relates to immunogenic compositions and methods of enhancing an immune response to an antigen. In certain embodiments, the disclosure relates to virus-like carries comprising a TLR5 agonist on the exterior without an antigen.

3 Claims, 14 Drawing Sheets

Figure 2A:
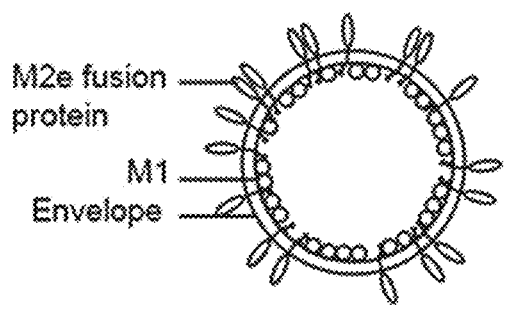

M2e sequence: (M) SLLTEVETPIRNEWGCRCNDSSDP
Sequence used:      SLLTEVETPIRNEWG S RS NDSSDP
4.M2e:
*AAA*SLLTEVETPIRNEWGSRSNDSSDP*AAGTSAAA*SLLTEVETPIRNEWGSRSNDSSDP*AAALQAAA*SLLTEVETPIRNEWGSRSNDSSDP*AAAACAAA*SLLTEVETPIRNEWGSRSNDSSDP*AAAACKL*

FIG. 1

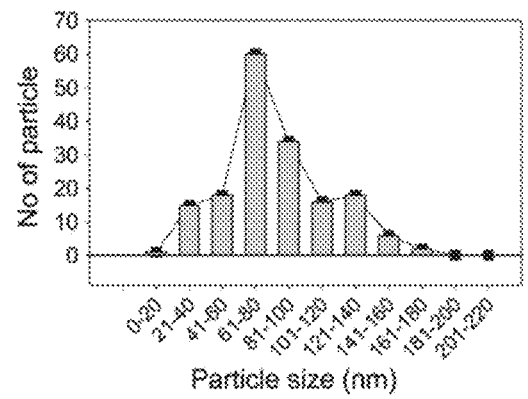
FIG. 9A                FIG. 9B
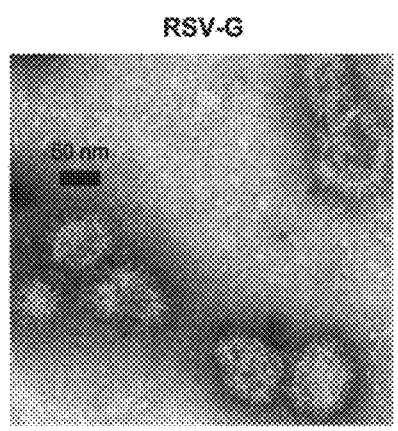
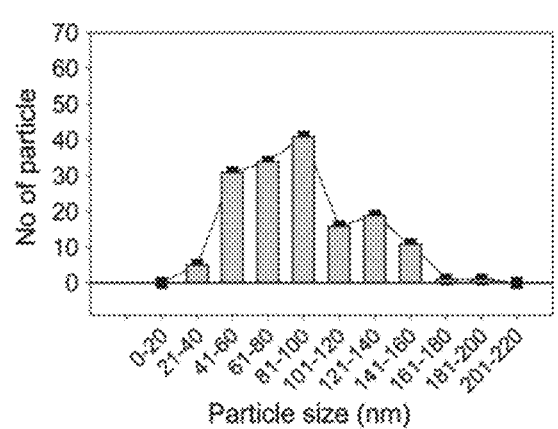
FIG. 9C                FIG. 9D
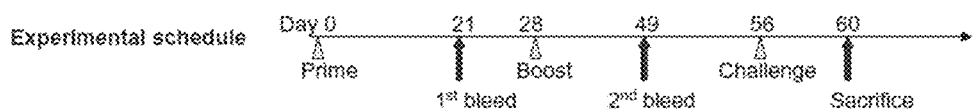
FIG. 10A

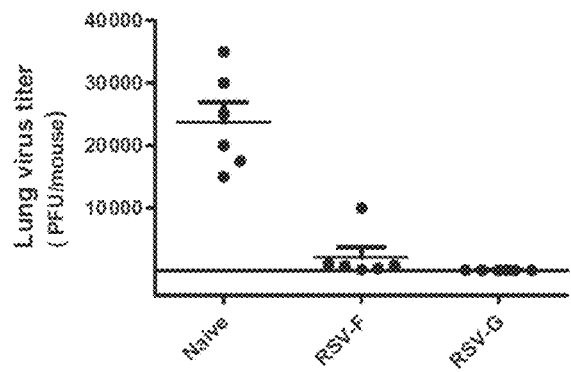
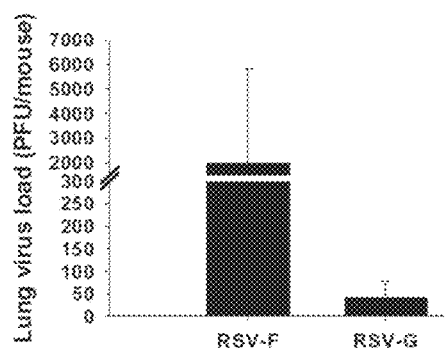
FIG. 14A          FIG. 14B
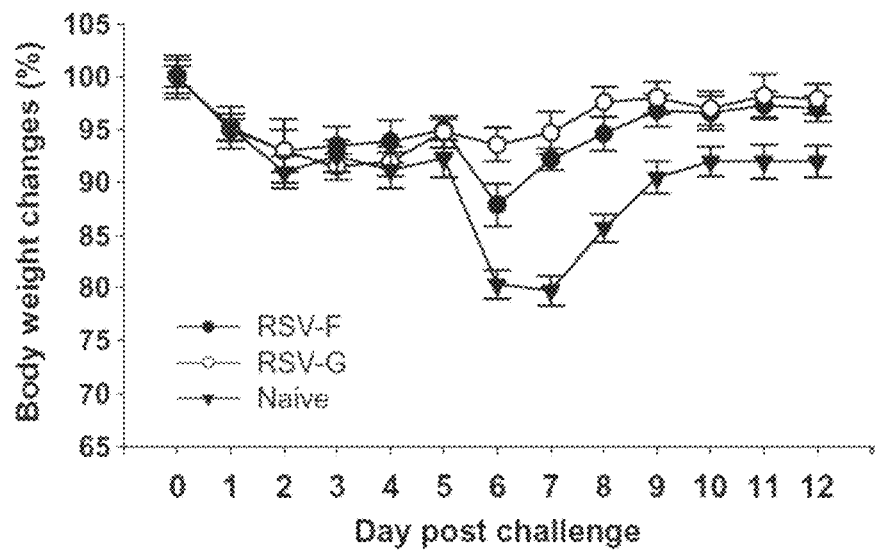
FIG. 14C

VLPS CONTAINING LIGANDS AND METHODS RELATED THERETO

CROSS-REFERENCE TO RELATED APPLICATIONS

This application claims priority to U.S. Provisional Application No. 61/513,695 filed 1 Aug. 2011, U.S. Provisional Application No. 61/513,905 filed 1 Aug. 2011, and U.S. Provisional Application No. 61/527,636 filed 26 Aug. 2011, all hereby incorporated by reference in their entirety.

STATEMENT REGARDING FEDERALLY FUNDED RESEARCH

This invention was made with government support under Grants AI068003 and UL1RR025008 awarded by the National Institutes of Health; and 1R43AI091230, 1R01AI068003, and 1R01AI087798 by the National Institute of Allergy and Infectious Diseases. The government has certain rights in the invention.

BACKGROUND

Virus-like particle (VLP) vaccines are genetically engineered complexes of multiple copies of protein antigens in a particulate virus-like structure. Viral proteins presented as VLPs or recombinant vaccine are immunogenic. Methods of creating VLPs are provided in U.S. Patent Application Publication Number 2006/02167702. See also U.S. Patent Application Publication Numbers 2006/0088909; 2010/0047277; 2010/0196419; 2010/0330190; 2011/0097358; 2012/0052082, and U.S. Pat. No. 7,763,450.

Influenza is one of the most important viral diseases in humans, with significant medical and economic burdens. Vaccination is an effective approach for prevention of influenza infection. Available seasonal influenza vaccines are trivalent inactivated (killed) virus vaccines (TIV) or live, attenuated, trivalent influenza virus vaccine (LAIV). These vaccines are targeted to primarily induce neutralizing antibodies directed against the viral envelope protein HA as well as the NA of strains homologous to the virus used for vaccination. However, influenza viruses undergo changes in their surface protein over time, called antigenic drift, allowing them to evade the host immune system and to reduce the effectiveness of immunity to prior infections. Such drifted strains can compromise vaccine-induced immunity due to antigenic mismatch with the vaccine strain, and the resulting seroprotection rates can vary according to the antigenic distance between the vaccine strain and the circulating strain. In addition, unexpected occurrence of shifted strains (resulting from the replacement of HA and less frequently NA subtypes with novel ones) may cause influenza pandemics. Major limitations of the current vaccines include the need to produce new vaccines every season, uncertainty in choice of the correct strains, long production times as well as the fact that the vaccines are produced by a slow process requiring embryonated eggs. Also, the current vaccines do not protect against future influenza pandemics. Improved vaccines are therefore needed, not only for seasonal influenza, but also for potential new influenza pandemic strains.

Because of these limitations of current vaccines, a universal vaccine that is based on relatively conserved protein domains would be a promising approach. A precondition is the accessibility to antibodies of these domains on infectious virus particles, intact infected cells, or both. The M2 protein of influenza A viruses is a tetrameric type III membrane protein, exhibiting pH-dependent proton transport activity. It is expressed at high density on the plasma membrane of infected cells, and its conserved extracelluar domain (M2e) is accessible to M2e-specific antibodies. However, because only a few copies of M2 are incorporated into the envelope of influenza viruses and the small M2e is shielded by the large surface HA and NA from efficient interaction with immune effector cells, M2e is poorly immunogenic although it is highly conserved. Studies have shown that, although M2e-specific antibodies were not able to prevent infection, they restricted subsequent virus replication and reduced illness and deaths. See Treanor et al., J Virol, 1990, 64(3): 1375-7.

The bacterial flagellar antigen flagellin is the natural ligand of Toll-like receptor (TLR) 5. Also, it can be recognized by an intracellular receptor Ipaf. It can be used as an adjuvant when co-administered with antigen in a physically associated form or mixture. As a protein adjuvant, flagellin can be genetically modified to produce different vaccine formulations. It has known that, in most isolates of Salmonella, two genes encode flagellar antigens. FliC encodes the phase I flagellin FliC, and fljB encodes the phase II flagellin FljB. These genes are coordinately expressed by a phase-variation mechanism. Both FliC and FljB share conserved N- and C-termini which form the flagellar filament backbone, and contain motifs recognized by cell surface TLR5 and cytoplasmic Ipaf.

A membrane-anchored form of the Salmonella Typhimurium phase I flagellin (FliC) can be co-incorporated into influenza VLPs as an adjuvant molecule. See U.S. Patent Application Publication No. 2010/0330190 and Wang et al., J Virol, 2008, 82(23):11813-23. The variable central region of FliC has been found to be unnecessary for its TLR5 binding activity. See Smith et al., Nat Immunol, 2003, 4(12):1247-53. Huleatt et al. Vaccine 2008; 26(2):201-14 disclose a universal influenza vaccine candidate comprising a recombinant fusion protein linking influenza M2e to the phase II flagellin (FljB). WO/2009/079564 discloses virus-like particles and a membrane-anchored flagellin constructed having repeats of M2e. Wang et al., PLoS One., 2010, 5(11):e13972, disclose that intranasal immunization with influenza VLPs incorporating membrane-anchored flagellin induces strong heterosubtypic protection.

Respiratory syncytial virus (RSV) is the leading cause of lower respiratory tract illness in infants and children worldwide. RSV has 10 genes encoding 11 proteins. The RSV fusion (F) and attachment glycoprotein (G) contain neutralizing antibody epitopes and several T-cell epitopes. See Olson & Varga, Expert Rev Vaccines, 2008; 7:1239-55, Moore et al., J Virol 2009; 83:4185-94, and U.S. Patent Application Publication Number 2011/0097358.

References cited herein are not an admission of prior art.

SUMMARY

This disclosure relates to immunogenic compositions and methods of enhancing an immune response to an antigen. In certain embodiments, the disclosure relates to virus-like carrier comprising a TLR5 agonist on the exterior without an antigen. In certain embodiments, the disclosure relates to methods of vaccinating a subject comprising administering an antigen in combination with a virus-like carrier comprising a TLR5 agonist wherein the virus-like carrier does not contain the antigen under conditions such that antibodies and/or memory B or T cells are produced in a sufficient quantity to prevent near future infection in a healthy human subject, subject over 50, 60, or 65 years of age, or a subject under 4, 8, or 12 years of age. In certain embodiments, the antigen is a viral, bacterial, fungal, or parasite derived molecule.

In certain embodiments, the disclosure relates to methods of immunizing a subject against a virus comprising administering an antigen in combination with a virus-like carrier comprising a TLR5 agonist to the subject. In certain embodiments, the TLR5 agonist is a flagellin in a membrane-anchored form, e.g., is FliC or FliC with the deletion of the variable region. In certain embodiments, the antigen is not a part of the virus-like carrier but administered in combination with the virus-like carrier. In certain embodiments, the antigen is a molecule with repeating units connected by linking groups. In certain embodiments, the antigen comprises an influenza protein such as M2e or a repeating sequence of M2e, e.g., an M2e sequence repeated 2, 3, 4, 5, or 6 or more times. Typically, the M2e cysteine amino acids, i.e., cysteine amino acid of the protein, are replaced with serine or alanine amino acids.

In certain embodiments, the antigen is an M2e polypeptide comprising SEQ ID NO: 1 or fragment thereof. In certain embodiments, the fragment is four, five, or six or more contiguous amino acids in SEQ ID NO: 1. In certain embodiments, the antigen comprises the M2e polypeptide SLLTEVETPIRNEWGSRSNDSSD (SEQ ID NO: 29), SLLTEVETPIRNEWGSRSNDSS (SEQ ID NO: 30), SLLTEVETPIRNEWGSRSNDS (SEQ ID NO: 31), SLLTEVETPIRNEWGSRSND (SEQ ID NO: 32), SLLTEVETPIRNEWGSRSN (SEQ ID NO: 33), SLLTEVETPIRNEWGSRS (SEQ ID NO: 34), SLLTEVETPIRNEWGSR (SEQ ID NO: 35), SLLTEVETPIRNEWGS (SEQ ID NO: 36), SLLTEVETPIRNEWG (SEQ ID NO: 37), SLLTEVETPIRNEW (SEQ ID NO: 38), SLLTEVETPIRNE (SEQ ID NO: 39), SLLTEVETPIRN (SEQ ID NO: 40), SLLTEVETPIR (SEQ ID NO: 41), SLLTEVETPI (SEQ ID NO: 42), SLLTEVETP (SEQ ID NO: 43), SLLTEVET (SEQ ID NO: 44), SLLTEVE (SEQ ID NO: 45), SLLTEV (SEQ ID NO: 46), SLLTE (SEQ ID NO: 47), SLLT (SEQ ID NO: 48), LLTE (SEQ ID NO: 49), LLTEV (SEQ ID NO: 50), LLTEVE (SEQ ID NO: 51), LLTEVET (SEQ ID NO: 52), LLTEVETP (SEQ ID NO: 53), LLTEVETPI (SEQ ID NO: 54), LLTEVETPIR (SEQ ID NO: 55), LLTEVETPIRN (SEQ ID NO: 56), LTEV (SEQ ID NO: 57), LTEVE (SEQ ID NO: 58), LTEVET (SEQ ID NO: 59), LTEVETP (SEQ ID NO: 60), LTEVETPI (SEQ ID NO: 61), LTEVETPIR (SEQ ID NO: 62), LTEVETPIRN (SEQ ID NO: 63), TEVE (SEQ ID NO: 64), TEVET (SEQ ID NO: 65), TEVETP (SEQ ID NO: 66), TEVETPI (SEQ ID NO: 67), TEVETPIR (SEQ ID NO: 68), TEVETPIRN (SEQ ID NO: 69), EVET (SEQ ID NO: 70), EVETP (SEQ ID NO: 71), EVETPI (SEQ ID NO: 72), EVETPIR (SEQ ID NO: 73), EVETPIRN (SEQ ID NO: 74), VETPI (SEQ ID NO: 75), VETPIR (SEQ ID NO: 76), VETPIRN (SEQ ID NO: 77), ETPI (SEQ ID NO: 78), ETPIR (SEQ ID NO: 79), ETPIRN (SEQ ID NO: 80), or TPIRN (SEQ ID NO: 81).

In certain embodiments, the antigen is a live attenuated virus or killed virus, i.e., inactivated vaccine. In certain embodiments, the flagellin is FliC or FliC wherein the variable region is absent and the virus-like carrier does not contain the antigen, i.e., a virus-like carrier consisting essential of a flagellin as an adjuvant. In certain embodiments, the disclosure relates to virus-like carries comprising flagellin sequences disclosed herein. In certain embodiments, the antigen and virus-like carrier are administered intra-nasally or intra-muscularly.

In certain embodiments, the disclosure relates to pharmaceutical compositions comprising virus-like carriers comprising a flagellin on the exterior without an antigen for uses disclosed herein. In certain embodiments, the disclosure relates to uses of virus-like carriers disclosed herein in the production of a medicament for the treatment or prevention of a viral infection.

In certain embodiments, the disclosure relates to immunogenic compositions comprising an antigen and/or a virus like carrier comprising a flagellin wherein the virus-like carrier comprising a TLR5 agonist wherein the virus-like carrier does not contain the antigen. The antigen may be a viral protein, such as M2e wherein the M2e cysteine amino acids are replaced with serine amino acids. The antigen is a repeating polypeptide sequence connected by linking groups. The TLR5 agonist may be a flagellin or a flagellin is FliC or FliC wherein the variable region is absent, e.g., polypeptides disclosed herein such as of SEQ ID NO: 28.

In certain embodiments, the disclosure relates to an immunogenic composition comprising a virus-like carrier having an influenza virus matrix protein and a RSV protein or glycoprotein on the surface. In certain embodiments, the influenza virus matrix protein is M1. In certain embodiments, the RSV protein is the F or G protein. In certain embodiments, the immunogenic composition further comprises a virus-like carrier comprising a TLR5 agonist, e.g., flagellin. In certain embodiments, the flagellin is FliC or FliC wherein the variable region is absent. In certain embodiments, the virus-like carrier comprises flagellin and the RSV protein or glycoprotein in the same virus-like carrier. In certain embodiments, the virus-like carrier comprises flagellin and does not contain the RSV protein or glycoprotein. In certain embodiment, the virus-like carrier is a virus-like particle.

In certain embodiments, the disclosure relates to methods of vaccinating a subject comprising administering an virus-like carrier having influenza virus matrix protein and a RSV protein on the surface in combination with a virus-like carrier comprising a TLR5 agonist. Typically the influenza virus matrix protein is M1 and the RSV protein is the F or G protein. Typically, the TLR5 agonist is a flagellin, e.g., FliC or FliC wherein the variable region is absent. In certain embodiments, the virus-like carrier comprising flagellin and the RSV protein or glycoprotein are in the same virus-like carrier. In certain embodiments, the virus-like carrier comprising flagellin does not contain the RSV protein or glycoprotein. Typically, the virus-like carrier is a virus-like particle.

In certain embodiments, the disclosure relates to immunogenic compositions comprising a virus-like carrier having influenza virus matrix protein wherein influenza virus matrix protein is M1 and a RSV protein is G protein or glycoprotein, optionally containing flagellin, on the surface in the absence of the F protein or glycoprotein.

An RSV-G virus-like particle produced by infecting insect cells, e.g., Sf9 or Sf21 cells, with a recombinant virus, e.g, rBVs, encoding RSV-G and M1, optionally containing a gene encoding a flagellin, and not the RSV-F gene.

In certain embodiments, the disclosure relates to methods of vaccinating a subject comprising administering an immunogenic composition disclosed herein. In certain embodiments, the subject is a human.

In certain embodiments, the disclosure relates to nucleic acid sequences encoding polypeptides disclosed herein.

BRIEF DESCRIPTION OF THE FIGURES

FIG. 1 shows the amino acid sequences and schematic diagram of constructs. The M2e sequence shown is the consensus of human influenza A virus M2e. Cysteines at sites 17 and 19 were substituted by serine amino acids. In 4.M2e, four repetitive M2e regions (the underlined sequences) are located in a tandem. Sequences in italics are flexible linkers. In the 4.M2e-tFliC fusion protein, the central immunogenic region of FliC (domain 3, D3, Aa177-401) was replaced by the 4.M2e sequence. In the membrane-anchored 4.M2e-tFliC, the mellitin signal peptide (SP) was fused to the N-terminus of 4.M2e-tFliC (the N-terminal domains 1 and 2, ND1-2, in FliC) to enable its ectodomain to reach the exocytic pathway, and is removed in the mature protein by insect cell signal peptidase. The transmembrane and cytoplasmic domains (TM/CT) of A/PR8 HA were attached to the C-terminus of the 4.M2e-tFliC fusion protein (the C-terminal domains 2 and 1, CD2-1, in FliC).

FIG. 2 shows data on the characterization of fusion proteins and M2e VLPs. A. Diagram of M1-derived VLPs. The membrane-anchored form of 4M2e-tFliC fusion protein is inserted into the bilayer lipid of the envelope; B. EM of a VLP; C, D and E. Characterization of VLPs. VLP samples were applied to SDS-PAGE followed by western blotting analysis. Lane 1, 4.M2e-tFliC/M1 VLPs; lane 2, FliC/M1 VLPs; lane 3, M1 VLPs. Protein bands were detected by: C, anti-FliC; D, anti-M2e (14C2); E, anti-M1 antibodies; F. TLR5 agonist activity of flagellin in fusion proteins or VLPs. The mouse macrophage cell line RAW264.7 which expresses TLR-2 and -4 without TLR-5 was used to determine the bioactivity of M2e-flagellin fusion protein or flagellin-containing VLPs. TLR-5 expressing RAW264.7 cells were prepared by transfection with the vector pUNO-hTLR5 expressing the human TLR-5. Data represent means±standard errors from triplicate repeats.

FIG. 3 shows data on serum IgG endpoint titers (A) and M2-specific IgG-binding (B). A. To determine serum IgG titers, ELISA assay plates were coated with 100 μl/well of synthesized M2e peptide (5 μg/ml). Immune sera 4 weeks after the last immunization were diluted in 2×steps, and 100 μl diluted samples were applied to plates for antibody-binding. Bound antibodies were detected by binding HRP-goat anti-mouse IgG antibody and color was developed with TMB substrate. The highest dilution which presented an OD450 2×higher than that of the negative control (naïve group) was designated as the endpoint titer. Representative data are the geometric mean (GM)±95% confidence interval (CI) of M2e-specific IgG titers of six mice in each group 4 weeks post the last immunization. B. Serum IgG recognizing native M2 protein was determined using cell surface ELISA. MDCK cells were infected with A/PR8 viruses at a MOI of 1. Uninfected cells were used as control. Twelve h postinfection, cells were washed with PBS and fixed with 10% formalin. Diluted samples were applied to detect antibody binding. Data depict the OD450 (mean±SD) of infected cells subtracting the background of uninfected cells. Groups 1 to 4 represent mouse groups immunized with 4.M2e, 4.M2e-tFliC, 4.M2e-tFliC/M1 VLPs, and 4.M2e plus FliC/M1 VLPs, respectively. $P<0.05$ (*), $P<0.01$ (*), $P<0.001$ (***).

FIG. 4 shows data on secretory IgA (A) and IgG (B) endpoint titers in immunized mouse lung lavages. Four weeks after the last immunization, lungs were collected and lavaged twice with 1 ml PBS containing 0.05% Tween 20 per lung. A. sIgA endpoint titers were determined as described for serum IgG endpoint titer in FIG. 3A but the secondary antibody used was HRP-conjugated goat anti-mouse IgA antibody. B. IgG titers were determined as described for serum IgG titers. Representative data are the GM±95% CI of six mice in each group.

FIG. 5 shows data on A/Philippines (H3N2) live virus challenge. Four weeks after the last immunization, 6 mice of each group were i.n. infected with $5\times LD_{50}$ of mouse-adapted A/Philippines viruses (250 pfu). Mouse survival (A) and body weight changes (B) were monitored and recorded for 15 days to indicate the protective efficacy of vaccines. In B, data represent means of the body-weight change (percentage of pre-challenge) of 6 mice in each group.

FIG. 6 shows data on A/PR8 (H1N1) virus challenge. Four weeks after the last immunization, mice were i.n. infected with 5×LD50 of mouse-adapted A/PR8 (125 pfu). Mouse survival (A) and body weight changes (B) were monitored and recorded as described in FIG. 5.

FIG. 7 shows data on lung viral load on day 4 postchallenge. Four weeks after the last immunization, three mice in each group were i.n. infected with 5LD50 of mouse-adapted PR8 (H1N1) or Philippines (H3N2) viruses. Mouse lungs were collected on day 4 postchallenge. Each lung was ground and cleared in 1 ml of DMEM. Virus titers of lung extracts were titrated using a standard plaque assay with MDCK cells. Lung viral titer was expressed as pfu/lung. Data depict the geometric means±95% CI of three mice from each group. Groups 1 to 4 represent mouse groups i.m. or i.n. immunized with 4.M2e, 4.M2e-tFliC, 4.M2e-tFliC/M1 VLPs, and 4.M2e plus FliC/M1 VLPs, respectively.

FIG. 8 shows data on characterization of virus-like particles (VLPs)-constructs of pFastBac vectors. Respiratory syncytial virus (RSV) fusion F gene (A), attachment glycoprotein G gene (B), and influenza M1 genes (C) are in pFastBac vectors. Genes were amplified by PCR or RT-PCR. Sizes of F, G, and M1 in vectors were confirmed by cutting with EcoRI and XhoI, and the nucleotide sequences were confirmed by DNA sequencing. VLPs containing M1 and RSV F (D) or RSV G (E) were purified from SF9 cell culture supernatants by sucrose gradient ultracentrifugation and visualized by Western blots. The 20, 5, and 1 μg VLPs were loaded per lane as indicated (D, E).

FIG. 9 shows virus-like particles (VLPs) containing M1 and respiratory syncytial virus (RSV) F (A) or RSV G (C) visualized and their size distribution determined (B, D) after negative staining EM (H-7500, Hitachi). Fifty-five (55%) of RSV F VLPs from 170 particles were distributed between 60 and 100 nm (B), and 66% of RSV-G VLPs from 161 particles were distributed between the size 40 and 100 nm (D).

FIG. 10 shows an experimental schedule and respiratory syncytial virus (RSV)-A2-specific antibody responses to RSV-F or RSV-G virus-like particles (VLPs). A, Groups of mice were intramuscularly immunized twice as indicated with a 4-week interval. At 4 weeks after boost, mice were challenge infected with RSV-A2 virus, and at day 4 after challenge mouse lungs were collected to determine lung virus loads. Enzyme-linked immunosorbent assay (ELISA) plates were coated with whole RSV virus. Serially diluted sera were used after prime and boost. Total immunoglobulin (Ig) G (B), isotypes IgG2a (C), IgG1 (D) responses, and the ratio of IgG2a to IgG1 (E) to RSV-F VLPs, and total IgG (F), isotype IgG2a (G), IgG1 (H), and the ratio of IgG2a to IgG1 (I) to RSV-G VLPs were determined from mice immunized with RSV-F VLPs.

FIG. 11 shows data on respiratory syncytial virus (RSV) A2-specific immunoglobulin (Ig) G, IgG2a, and IgG1 responses and the ratio of IgG2a to IgG1 in lung extract samples collected at day 4 postchallenge. Serially diluted lung samples were used to determine IgG (A, C), IgG2a, and IgG1 (B, D) responses and the ratio (E) in mice immunized with RSV-F virus-like particles (VLPs) or immunized with RSV-G VLPs.

FIG. 12 shows data on immunoglobulin (Ig) G, IgG1, and IgG2a responses against cell surface expressed respiratory syncytial virus (RSV)-A2 proteins. HEp-2 cells in 96 well culture plates were infected with RSV A2 as described in Methods. Serially diluted mouse sera were added into wells. IgG, IgG2a, and IgG1 responses were determined from mice immunized with RSV-F virus-like particles (VLPs) (A, B) or immunized with RSV-G VLPs (D, E). Total IgG responses were also determined by enzyme-linked immunosorbent assay (ELISA) by using HEp-2 cells infected with RSV A2 or uninfected controls. Sera were obtained at week 2 after prime from mice immunized with RSV-F VLPs (C) or RSV-G VLPs (F).

Figure 13:
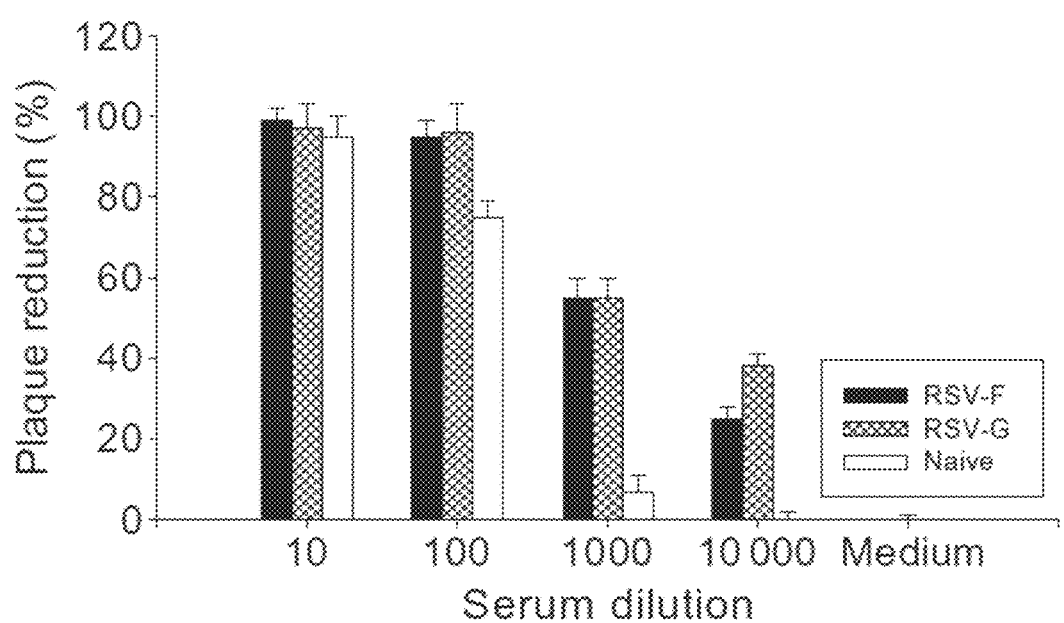

FIG. 13 shows data on serum neutralizing activities. Complement inactivated mouse sera were tested for inhibition of respiratory syncytial virus (RSV)-A2 plaque formation. Serially diluted mouse sera at week 3 after boost were complement inactivated and incubated with live RSV-A2. Virus was diluted and used at 750 PFU/well.

FIG. 14 shows data on lung virus loads and body weight changes after respiratory syncytial virus (RSV)-A2 challenge. The experiment was repeated twice. A, Lung virus load. Lungs from individual mice in each group (6 mice) were collected on day 4 post-challenge, and lung virus loads (number of plaque-forming units [PFU]) in each mouse were determined. The limit of virus detection is 50 PFU/mL. B, Comparison of lung virus loads between RSV-F and RSV-G virus-like particles (VLPs). The lower scale of the Y axis was used to see differences in lung virus loads between RSV-F and RSV-G VLP immunization. C, Body weight changes. Vaccinated mice (6 mice) were challenged with live RSV-A2 virus. The body weights were monitored daily in which 100% body weight was seen at day 0.

DETAILED DISCUSSION

Influenza

Current influenza vaccines induce neutralizing antibodies against the HA and to a lesser extent to the NA protein, and are protective against closely matched virus strains. However the rapid appearance of mutations allows the virus to evade preexisting anti-influenza immunity. The possibility of adaption of a highly pathogenic avian virus to humans also adds to the risk of the current influenza vaccine strategy.

In certain embodiments, disclosure contemplates uses of a broad protective efficacy of influenza vaccine candidates which include epitopes such as the extracellular domain of the influenza M2 protein (M2e). M2e is conserved in all A type influenza viruses. A systematic approach was used to target M2e for the development of a universal influenza vaccine. Firstly, a fusion protein (4.M2e-tFliC) was generated by replacing the variable region of FliC with multiple M2e peptides (4.M2e). Second, a membrane-anchor was genetically attached from the influenza HA to the 4.M2e-tFliC fusion protein and this membrane-anchored form was incorporated into M1-derived VLPs. VLPs are advantageous as immunogens in inducing strong immune responses because they mimic the structures of viruses which the immune system has evolved to fight.

The HA cytoplasmic domain contains signals guiding the envelope glycoprotein to assemble into M1-derived VLPs. A fusion protein with an HA membrane-anchor can be incorporated into M1-derived VLPs. M2e may to be delivered in a particulate form, and to be presented in its native external-membrane-microenvironment. This enables the use of a particulate form of FliC (FliC VLPs) as adjuvant to enhance the immune responses induced by the multiple M2e peptides. Although the use of tandem repeats increases the density of the target epitopes in a molecule, a possible concern is that the antibody responses induced may not recognize the native M2. Mozdzanowska et al., Vaccine 2003; 21 (19-20):2616-26, suggest that on average 10% of the total antibody responses induced by multiple M2e repeats cross-reacted with native M2 on virus-infected cell surface. However it has been discovered in the present study that in the right conditions M2e induces a high level of M2-specific immunity and complete protection against lethal doses of live virus challenges.

Because the variable region of FliC is hyperimmunogenic, an advantage of deleting or replacing of the variable region of FliC with M2e repeats avoids possible antibody-mediated neutralization of its TLR5 signaling. The specific innate TLR5 signaling activity of FliC may transform any appropriate foreign B cell determinant into a potentially strong immunogen.

Several different immunization routes have been used to deliver M2e-derived antigens for inducing protective immunity. I.n. immunization was found to be an advantageous approach in inducing protective immunity compared to the other routes. I.n. immunization with 4.M2e-tFliC fusion protein or VLPs induces high systemic immune responses as well as strong mucosal immunity, and confers more effective protection to live virus challenge as demonstrated by the complete protection against PR8 or Philippines challenge, and minimal body weight losses. Also, virus replication is restricted in lungs, as revealed by lower lung virus titers. I.n. immunization stimulates the nasopharyngeal-associated lymphoreticular tissue (NALT), and induces local mucosal immunity. Furthermore, the variable region-truncated flagellin has been found to be more efficient as a mucosal adjuvant as discussed above. These observations provide a basis for the finding that the specific M2e-tFliC fusion protein also contributes to enhanced mucosal immunity.

The most surprising discovery is that mice immunized with a mixture of 4.M2e plus FliC VLPs administered i.n. achieved the best immune responses.

Respiratory Syncytial Virus (RSV)

The protective efficacies of RSV vaccines produced in a viruslike particle form were investigated after intramuscular vaccination in a mouse model. VLP vaccination provides effective protection against RSV infection. RSV-F or RSV-G VLPs elicited significant levels of IgG2a-dominant RSV-specific IgG antibody responses and significantly reduced lung viral replication and weight loss upon challenge.

The VLPs targeted the full-length RSV fusion F protein (RSV-F) and attachment G glycoprotein (RSV-G) which possess neutralizing epitopes as well as several T-cell epitopes. Influenza M1 protein was used rather than RSV matrix (M) as a core protein in VLPs because matrix proteins are important for virion morphology and RSV is more pleomorphic than influenza virus. Also, some paramyxovirus M proteins are insufficient for VLP formation in the absence of NP and envelope glycoprotein co-expression. RSV-F or RSV-G VLPs showed spherical particle shapes. The rBV-produced VLP vaccines from serum-free insect cells have advantages over VLPs produced in mammalian cells because mammalian cell-produced VLPs need to be validated to be free of viruses or oncogenic substances originating from the cells and/or serum.

It has been reported that an RSV VLPs vaccine containing RSV-G protein induces protection in a mouse model. See Murawski et al., J Virol 2010; 84:1110-23. In this report, a chimeric protein was used in which the ectodomain was from the RSV G protein, but the cytoplasmic and transmembrane domains and M protein were from Newcastle disease virus (NDV). IgG subtype responses from vaccination with these VLPs were not determined.

The currently disclosed experiments focused on the full length RSV-F or -G proteins in VLPs. The RSV-G VLPs induced better protection than RSV-F VLPs. RSV-F does not require other viral proteins for fusion activity and can undergo pre- to postfusion triggering upon expression. It is not intended that certain embodiments, be limited by any particular mechanism; however, it is possible that some F on the VLP surface may be in a postfusion form, potentially underrepresented on the challenge virus. Alternatively, RSV-F and/or -G may be differentially glycosylated in insect cells used to produce the VLPs, compared with mammalian cells and the underglycosylation of G may enable immune focusing on protectopes (e.g., the central region of G). RSV-F VLPs will provide protection against RSV isolates of A and B subgroups, whereas protection induced by RSV-G VLPs may be more subgroup-specific. In mice and cotton rats, subgroup-heterologous protection is readily achievable with F antigen immunization, and significant but partial subgroup-heterologous protection is typically observed with RSV G antigens. Within antigenic subgroups, RSV can be further classified into clades based on sequence analyses of a hypervariable carboxy-terminus region of RSV G.

An ELISA assay was developed to detect IgG, IgG2a, and IgG1 antibodies by using cell surface expressed RSV proteins. Since a correlation of antibody responses with protection was found using cell surface RSV-A2 proteins as binding antigens, detecting antibody using this method may be more reliable and will contribute to RSV vaccine studies. RSV-F and RSV-G VLP vaccines induced very high levels of IgG2a isotype responses with very low levels of IgG1 isotype responses. This is encouraging since enhanced disease after RSV challenge is reported to be related to Th2 (IgG1) allergy-like or Th2-associated responses. It has been reported that F and G protein subunit RSV vaccines were weakly immunogenic and caused enhanced pulmonary histopathology. In contrast, Venezuelan equine encephalitis virus replicon particles (VRPs), as well as RSV G-expressing Newcastle disease VLPs, were more immunogenic, effective, and did not cause enhanced RSV disease. Since RSV proteins in VLPs are presented in a repetitive, particulate virus-like structure, they may be highly immunogenic and induce protective humoral, cellular, and mucosal immune responses.

This is believed to be the first report demonstrating and comparing protection induced by VLPs containing full-length fusion (F) or attachment (G) glycoproteins. RSV-F or RSV-G VLPs successfully inhibit virus replication in the lung and protected mice from infection. RSV-F or RSV-G VLPs are promising vaccine candidates.

Terms

As used herein, "a flagellin" refers to the monomer subunit in flagella, e.g., flagellin gene product of FliC and FljB in S. typhimurium and FlaA in L. pneumophila, or variants, analogs, derivatives, fragments or combination thereof, such as a domain or polypeptide sequence in the domain. Typically, the flagellin monomer contains D0, D1, D2, and D3 domains. An alignment of the amino acid sequences from different Gram-negative species shows a high degree of similarity in the amino and carboxy terminal domains. The central regions of these proteins may be quite divergent. Smith, K. D., et al, Nature Immunol. (2003) 4:1247-1253 disclose that TLR5 recognizes a site on the flagellin of Salmonella typhimurium (FliC) composed of N-terminal residues 78-129 and 135-173 and C-terminal residues 395-444. The term "a flagellin" is not intended to be limited to any particular amino acid sequence provided that it has some homology to known flagellin sequences and the molecule retains the ability to stimulate innate immune responses. The innate immune responses of flagellin are known to includes cytokine production in response to TLR (including TLR5) activation and activation of Caspase-1 and IL-1β secretion in response to certain NLRs (including Ipaf). In certain embodiments, a flagellin is contemplated to include additional amino acids within the sequence, such as in the case of fusion or chimeric proteins, provided that these proteins continue to affect an innate immune response that comprises a TLR5-mediated immune response, an Ipaf-mediated immune response or both. Also specifically contemplated are fragments, variants, analogs, homologs, or derivatives of said flagellin, and combinations thereof provided these molecules continue to affect an innate immune response that comprises a TLR5-mediated immune response, an Ipaf-mediated immune response or both. A flagellin may be isolated from natural sources, by synthetic or recombinant technologies or combinations thereof.

Individual salmonella serotypes usually alternate between the production of two forms of flagellin, termed phase 1 and phase 2, each specified by separate structural genes FliC and FljB. The amino acid sequences of phase-1 flagella protein of salmonella typhimurium (FliC) is set forth in SEQ ID NO: 12, MAQVINTNSL SLLTQNNLNK SQSALGTAIE RLSS- GLRINS AKDDAAGQAI ANRFTANIKG 61 LTQASR- NAND GISIAQTTEG ALNEINNNLQ RVRELAVQSA NSTNSQSDLD SIQAEITQRL 121 NEIDRVSGQT QFNGVKVLAQ DNTLTIQVGA NDGETIDIDL KQIN- SQTLGL DTLNVQQKYK 181 VSDTAATVTG YADT- TIALDN STFKASATGL GGTDQKIDGD LKFDDTTGKY YAKVTVTGGT 241 GKDGYYEVSV DKTNGEVTLA GGATSPLTGG LPATATEDVK NVQVANADLT EAKAALTAAG 301 VTGTASVVKM SYTDNNGKTI DGGLAVKVGD DYYSATQNKD GSISINTTKY TAD- DGTSKTA 361 LNKLGGADGK TEVVSIGGKT YAAS- KAEGHN FKAQPDLAEA AATTTENPLQ KIDAALAQVD 421 TLRSDLGAVQ NRFNSAITNL GNT- VNNLTSA RSRIEDSDYA TEVSNMSRAQ ILQQAGTSVL 481 AQANQVPQNV LSLLR.

The amino acid sequences of phase-2 flagella protein of salmonella typhimurium (FljB) is set forth in SEQ ID NO: 13, MAQVINTNSL SLLTQNNLNK SQSALGTAIE RLSS- GLRINS AKDDAAGQAI ANRFTANIKG 61 LTQASR- NAND GISIAQTTEG ALNEINNNLQ RVRELAVQSA NSTNSQSDLD SIQAEITQRL 121 NEIDRVSGQT QFNGVKVLAQ DNTLTIQVGA NDGETIDIDL KQIN- SQTLGL DSLNVQKAYD 181 VKDTAVTTKA YANNGT- TLDV SGLDDAAIKA ATGGTNGTAS VTGGAVKFDA DNNKYFVTIG 241 GFTGADAAKN GDYEVNVATD GTVTLAAGAT KTTMPAGATT KTEVQELKDT PAV- VSADAKN 301 ALIAGGVDAT DANGAELVKM SYTD- KNGKTI EGGYALKAGD KYYAADYDEA TGAIKAK- TTS 361 YTAADGTTKT AANQLGGVDG KTEVVTIDGK TYNASKAAGH DFKAQPELAE AAAK- TTENPL 421 QKIDAALAQV DALRSDLGAV QNRFN- SAITN LGNTVNNLSE ARSRIEDSDY ATEVSNMSRA 481 QILQQAGTSV LAQANQVPQN VLSLLR.

The amino acid sequences of F41 fragment of flagellin of salmonella typhimurium is set forth in SEQ ID NO: 14, FTANIKGLTQ ASRNANDGIS IAQTTEGALN EINNN-LQRVR ELAVQSANST NSQSDLDSIQ 61 AEITQRLNEI DRVSGQTQFN GVKVLAQDNT LTIQVGANDG ETI-DIDLKQI NSQTLGLDTL 121 NVQQKYKVSD TAAT-VTGYAD TTIALDNSTF KASATGLGGT DQKIDGDLKF DDTTGKYYAK 181 VTVTGGTGKD GYYEVSVDKT NGEVTLAGGA TSPLTGGLPA TATEDVKNVQ VANADLTEAK 241 AALTAAGVTG TASVVKMSYT DNNGKTIDGG LAVKVGDDYY SATQNKDGSI SINTT-KYTAD 301 DGTSKTALNK LGGADGKTEV VSIGGK-TYAA SKAEGHNFKA QPDLAEAAAT TTENPLQKID 361 AALAQVDTLR SDLAAVQNRF NSAITNLGNT VNNLTSAR.

The amino acid sequences of a flagellin fusion protein is set forth in SEQ ID NO:15, MALTVNTNIA SLNTQRN-LNN SSASLNTSLQ RLSTGSRINS AKDDAAGLQI ANRLTSQVNG 61 LNVATKNAND GISLAQTAEG ALQQSTNILQ RMRDLSLQSA NGSNSDSERT ALN-GEVKQLQ 121 KELDRISNTT TFGGRKLLDG SFGVAS-FQVG SAANEIISVG IGGGKLMIKL KFGVFFTVLL 181 SSAYAHGTPQ NITDLCAEYH NTQIHTLNDK IFSYTE-SLAG KREMAIITFK NGATFQVEVP 241 GSQHID-SQKK AIERMKDTLR IAYLTEAKVE KLCVWNNKTP HAIAAISMAN.

Polypeptide fragments of flagellin include SEQ ID NO: 16, GALNEINNNL QRVRELAVQ SANSTNSQS DLD-SIQAE ITQ; SEQ ID NO: 17, TQFSGVKVLAQDNTL-TIQVGANDGET IDIDLKQINS QTLGLDTL; SEQ ID NO: 18, EGALNEINN NLQRVRELA VQSANSTNS QSDLDSIQAEITQRLNEIDRVNG; SEQ ID NO: 19, MAQVINTNSL SLLTQNNLNK SQSALGTAI ERLSSGL-RINSAKDDAAGQAIANF TANIKGLTQA SRNANDGISI AQTTEGALN EINNNLQRVRELAVQS; SEQ ID NO: 20, LQKIDAALAQVDTLRSDLGAVQNRFNSAITNL; SEQ ID NO: 21, TLRSDLGAVQNRFNSAITNLGNTVNNLSS; and SEQ ID NO: 22, EQAAKTTEN PLQKIDAALAQVDTLRSDLGAVQNRFNSAITNLGNT-VNNLSS.

Combination of fragments of flagellin include SEQ ID NO: 23, Met Arg Gly Ser His His His His His His Gly Met Ala Ser Met Thr1 Gly Gln Gln Met Gly Arg Asp Leu Tyr Asp Asp Asp Asp Lys Asp Pro Met Ala Gln Val Ile Asn Thr Asn Ser Leu Ser Leu Leu Thr Gln Asn Asn Leu Asn Lys Ser Gln Ser Ser Leu Ser Ser Ala Ile Glu Arg Leu Ser Ser Gly Leu Arg Ile Asn Ser Ala Lys Asp Asp Ala Ala Gly Gln Ala Ile Ala Asn Arg Phe Thr Ser Asn Ile Lys Gly Leu Thr Gln Ala Ser Arg Asn Ala Asn Asp Gly Ile Ser Ile Ala Gln Thr Thr Glu Gly Ala Leu Asn Glu Ile Asn Asn Asn Leu Gln Arg Val Arg Glu Leu Ser Val Gln Ala Thr Asn Gly Thr Asn Ser Asp Ser Asp Leu Lys Ser Ile Gln Asp Glu Ile Gln Gln Arg Leu Glu Glu Ile Asp Arg Val Ser Asn Gln Thr Gln Phe Asn Gly Val Lys Val Leu Ser Gln Asp Asn Gln Met Lys Ile Gln Val Gly Ala Asn Asp Gly Glu Thr Ile Thr Ile Asp Leu Gln Lys Ile Asp Val Lys Ser Leu Gly Leu Asp Gly Phe Asn Val Asn Ser Pro Gly Ile Ser Gly Gly Gly Gly Gly Ile Leu Asp Ser Met Gly Thr Leu Ile Asn Glu Asp Ala Ala Ala Ala Lys Lys Ser Thr Ala Asn Pro Leu Ala Ser Ile Asp Ser Ala Leu Ser Lys Val Asp Ala Val Arg Ser Ser Leu Gly Ala Ile Gln Asn Arg Phe Asp Ser Ala Ile Thr Asn Leu Gly Asn Thr Val Thr Asn Leu Asn Ser Ala Arg Ser Arg Ile Glu Asp Ala Asp Tyr Ala Thr Glu Val Ser Asn Met Ser Lys Ala Gln Ile Leu Gln Gln Ala Gly Thr Ser Val Leu Ala Gln Ala Asn Gln Val Pro Gln Asn Val Leu Ser Leu Leu Arg. This protein is also known as CBLB502 (AA') as provided for in U.S. Published Patent Application No. 2009/0011982, hereby incorporated by reference. CBLB502 is currently under clinical investigation to treat Acute Radiation Syndrome (ARS).

As used herein, an "RSV G" protein, or like terms refers to attachment an RSV glycoprotein G and all known variants or substantial fragments thereof. One example is MSKNKDQRTA KTLERTWDTL NHLLFISSCL YKLN-LKSVAQ ITLSILAMII STSLIIAAII 61 FIASANHKVT PTTAIIQDAT SQIKNTTPTY LTQNPQLGIS PSNPSEITSQ ITTILASTTP 121 GVKSTLQSTT VKT-KNTTTTQ TQPSKPTTKQ RQNKPPSKPN NDFHFE-VFNF VPCSICSNNP 181 TCWAICKRIP NKKPGKKTTT KPTKKPTLKT TKKDPKPQTT KSKEVPTTKP TEEPTINTTK 241 TNIITTLLTS NTTGNPELTS QMET-FHSTSS EGNPSPSQVS TTSEYPSQPS SPPNTPRQ (SEQ ID NO: 88). Other examples include those designated by Accession numbers P03423.1, P27022.1, CAA51765.1, AAD02944.1, CAA83874.1, AAD02941.1, CAA83870.1, P27021.1, AEO45938.1, CAA51761.1, CAA83871.1, AAU43727.1, AEO45918.1, AEO45888.1, AEO45878.1, AEO45849.1, AEC32086.1, AEQ98767.1, AEQ63333.1, CAA83875.1, AEO45908.1, AEO45948.1, AEO45898.1, AEO45928.1, AAC36327.1, ACO83296.1, AEO45829.1, AEQ66845.1, ACI03570.1, AEO45868.1, P20895.2, AAD02943.1, AAX23993.1, AEQ66853.1, AEO45839.1, AEJ87998.1, and AEJ88006.1. The term "RSV G" is not intended to be limited to any particular amino acid sequence provided that it has substantial homology to a known RSV G sequences. Alternative glycosylations are contemplated. In certain embodiments, a known RSV G sequence has 2, 3, 4, 5, 6, 7, 8, or 9 amino acid substitutions or 2, 3, 4, 5, 6, 7, 8, or 9 amino acids have been deleted on the N or C terminal end of the polypeptide. In certain embodiments, a RSV G is contemplated to include additional amino acids within the sequence, such as in the case of fusion or chimeric proteins. In certain embodiments, variants may contain conserved amino acid substitutions or derivatives with common chemical groups such as protecting groups or halogens. In certain embodiments, the fragments are between 250 to 200, 200 to 150, 150 to 100, 100 to 50, or 25 amino acids.

As used herein, the term "adjuvant molecule" includes bacterial surface proteins capable of eliciting an immune response in a host. In particular the term includes bacterial surface proteins capable of targeting a host Toll-like receptor (TLR) protein, such as, but not limited to, a bacterial flagellin protein that targets a host TLR5 protein. In particular embodiments, the adjuvant molecule is a "membrane-anchored form" of the adjuvant molecule which indicates that the adjuvant molecule has been engineered to include a signal peptide (SP) and a membrane anchor sequence to direct the transport and membrane orientation of the protein. Thus, in embodiments, a membrane-anchored form of an adjuvant molecule is a recombinant protein including a portion of the bacterial protein (such as bacterial flagellin) fused to a SP and membrane anchor sequence.

The term "virus-like carrier" as used herein refers to a virus-like particle, a virosome, or both.

The term "virus-like particle" (VLPs) as used herein refers to a membrane-surrounded viral core structure having viral envelope proteins. In addition, adjuvant molecules can be expressed on the VLP. Further, viral core proteins are located within the membrane of the VLP. Additional components of VLPs, as known in the art, can be included within or disposed on the VLP. VLPs typically do not contain intact viral nucleic acids, and they are non-infectious.

The term "virosome" as used herein refers to a virus-like carrier that is similar to a virus-like particle, except that a virosome does not contain a viral core protein A "truncated" viral surface envelope glycoprotein is one having less than a full length protein (e.g., a portion of the cytoplasmic domain has been removed), which retains surface antigenic determinants against which an immune response is generated, preferably a protective immune response, and it retains sufficient envelope sequence for proper membrane insertion. The skilled artisan can produce truncated virus envelope proteins using recombinant DNA technology and virus coding sequences, which are readily available to the public.

The terms "proteins," "peptides," and "polypeptides" refer to the molecules created by coupling with amino acid residues, i.e., amino acid sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (GIn, Q), Glutamic Acid (GIu, E), Glycine (GIy, G), Histidine (His, H), lsoleucine (lie, I)1 Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (VaI, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e g, substitutions, additions, and/or deletions). A substituted or inserted ammo acid residue may or may not be one encoded by the genetic code. A variant of a polypeptide may be naturally occurring such as an allelic variant, or it may be a variant that is not known to occur naturally Modifications and changes can be made in the structure of the polypeptides of this disclosure and still result in a molecule having similar characteristics as the polypeptide (e g, a conservative amino acid substitution). For example, certain amino acids can be substituted for other amino acids in a sequence without appreciable loss of activity. Because it is the interactive capacity and nature of a polypeptide that defines that polypeptide's biological functional activity, certain ammo acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are isoleucine (+4.5), valine (+4.2), leucine (+3.8), phenylalanine (+2.8) cysteine/cysteine (+2.5) methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5) asparagine (−3.5), lysine (−3.9), and arginine (−4.5).

It is believed that the relative hydropathic character of the amino acid determines the secondary structure of the resultant polypeptide, which in turn defines the interaction of the polypeptide with other molecules, such as enzymes substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred Substitution of like ammo acids can also be made on the basis of hydrophilicity, particularly where the biologically functional equivalent polypeptide or peptide thereby created is intended for use in immunological embodiments. The following hydrophilicity values have been assigned to amino acid residues arginine (+3.0), lysine (+3.0), aspartate (+3.0) glutamate (+3.0), serine (+0.3), asparagine (+0.2), glutamine (+0.2), glycine (0), proline (−0.5), threonine (−0.4), alanine (−0.5), histidine (−0.5), cysteine (−1.0), methionine (−1.3), valine (−1.5) leucine (−1.8), isoleucine (−1.8), tyrosine (−2.3), phenylalanine (−2.5), and tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the ammo acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala. GIy, Ser), (Arg Lys), (Asn. GIn, His), (Asp: GIu1 Cys, Ser), (GIn. Asn), (GIu. Asp), (GIy. Ala), (His. Asn, GIn), (lie Leu, VaI), (Leu: lie, VaI), (Lys: Arg), (Met: Leu, Tyr), (Ser: Thr), (Thr: Ser), (Tip: Tyr), (Tyr: Trp, Phe), and (VaI-lie, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest. The term "substantially homologous" is used herein to denote polypeptides of the present disclosure having about 50%, about 60%, about 70%, about 80%, about 90%, and preferably about 95% sequence identity to the reference sequence. Percent sequence identity is determined by conventional methods as discussed above. In general, homologous polypeptides of the present disclosure are characterized as having one or more amino acid substitutions, deletions, and/or additions.

"Identity," as known in the art, is a relationship between two or more polypeptide sequences, as determined by comparing the sequences. In the art, "identity" also refers to the degree of sequence relatedness between polypeptides as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I1 Griffin, A. M., and Griffin, H. G., Eds., Humana Press, New Jersey, 1994, Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48. 1073, (1988). Preferred methods to determine identity are designed to give the largest match between the sequences tested. Methods to determine identity and similarity are codified in publicly available computer programs. The percent identity between two sequences can be determined by using analysis software (Sequence Analysis Software Package of the Genetics Computer Group, Madison, Wis.) that incorporates the Needelman & Wunsch (J Mol Biol, 48 443-453, 1970) algorithm (e.g., NBLAST and XBLAST). The default parameters are used to determine the identity for the polypeptides of the present disclosure. By way of example, a polypeptide sequence may be identical to the reference sequence, that is be 100% identical, or it may include up to a certain integer number of amino acid alterations as compared to the reference sequence such that the % identity is less than 100%. Such alterations are selected from at least one amino acid deletion, substitution (including conservative and non-conservative substitution), or insertion, and wherein said alterations may occur at the amino- or carboxy-terminus positions of the reference polypeptide sequence or anywhere between those terminal positions, interspersed either individually among the amino acids in the reference sequence, or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroprohne, 3- and 4-methylproline, 3,3-dimethylproline, tert-leucine, norvaline, 2-azaphenyl-alanine, 3-azaphenylalanine, 4-azaphenylalanine, and 4-fluorophenylalanine Several methods are known in the art for incorporating non-naturally occurring ammo acid residues into proteins For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E coli S30 extract and commercially available enzymes and other reagents. Proteins are purified by chromatography (Robertson, et al, J Am Chem Soc, 113 2722, 1991, Ellman, et al, Methods Enzymol, 202 301, 1991, Chung, et al, Science, 259 806-9, 1993, and Chung, et al, Proc Natl Acad Sci USA, 90 10145-9, 1993). In a second method, translation is carried out in Xenopus oocytes by microinjection of mutated mRNA and chemically aminoacylated suppressor tRNAs (Turcatti, et al, J Biol Chem, 271 19991-8, 1996). Within a third method, E coli cells are cultured in the absence of a natural amino acid that is to be replaced (e g, phenylalanine) and in the presence of the desired non-naturally occurring ammo acid(s) (e g, 2-azaphenylalanine 3-azaphenylalanine, 4-azaphenylalanine, or 4-fluorophenylalanine) The non-naturally occurring ammo acid is incorporated into the protein in place of its natural counterpart (Koide, et al, Biochem, 33 7470-6, 1994). Naturally occurring amino acid residues can be converted to non-naturally occurring species by in vitro chemical modification. Chemical modification can be combined with site-directed mutagenesis to further expand the range of substitutions (Wynn, et al, Protein Sci, 2 395-403, 1993).

Furthermore, unless the context demands otherwise, the term peptide, polypeptide and protein are used interchangeably to refer to amino acids in which the amino acid residues are linked by covalent peptide bonds or alternatively (where post-translational processing has removed an internal segment) by covalent disulphide bonds, etc. The ammo acid chains can be of any length and comprise at least two amino acids, they can include domains of proteins or full-length proteins. Unless otherwise stated the terms peptide, polypeptide, and protein also encompass various modified forms thereof, including but not limited to glycosylated forms, phosphorylated forms, etc.

By "administration" is meant introducing a composition (e g, a vaccine, adjuvant, or immunogenic composition) of the present disclosure into a subject. Any route of administration, such as oral, topical, subcutaneous, peritoneal, intra-arterial, inhalation, vaginal rectal, nasal, introduction into the cerebrospinal fluid, or instillation into body compartments can be used.

"Immunogenic compositions" are those which result in specific antibody production or in cellular immunity when injected into a subject. Such immunogenic compositions or vaccines are useful, for example, in immunizing against infection and/or damage caused by viruses.

By "immunogenic amount" is meant an amount capable of eliciting the production of antibodies directed against the virus, in the host to which the vaccine has been administered. It is preferred that the route of administration and the immunogenic composition is designed to optimize the immune response on mucosal surfaces for example, using nasal administration (via an aerosol) of the immunogenic composition.

The term "pharmaceutically" or "pharmaceutically acceptable" as used herein refer to molecular entities and compositions that do not produce an adverse, allergic or other untoward reaction when administered to an animal, or a human, as appropriate.

The term "pharmaceutically acceptable carrier" as used herein refers to any carrier, excipient, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients can also be incorporated into the compositions as suitable therapeutic combinations. The term "subject" as used herein includes humans, mammals (e.g., cats, dogs, horses, etc.), and livestock. Typical subject to which embodiments of the present disclosure may be administered will be mammals, particularly primates, especially humans. For veterinary applications, a wide variety of subjects will be suitable, e.g., livestock such as cattle, sheep, goats, cows, swine, and the like, poultry such as chickens, ducks, geese, turkeys and the like, and domesticated animals particularly pets such as dogs and cats.

The term "treat", "treating", and "treatment" are an approach for obtaining beneficial or desired clinical results. For purposes of embodiments of this disclosure, beneficial or desired clinical results include, but are not limited to, alleviation of symptoms, diminishment of extent of disease, stabilization (e g, not worsening) of disease, preventing spread of disease, delaying or slowing of disease progression, amelioration or palliation of the disease state, and remission (partial or total) whether detectable or undetectable. In addition, "treat," "treating," and "treatment" can also mean prolonging survival as compared to expected survival if not receiving treatment.

EXPERIMENTAL

Cell Lines and Viruses

Spodoptera frugiperda sf9 cells were maintained as described in Wang et al., J Virol, 2008, 82(23):11813-23 hereby incorporated by reference. Madin-Darby canine kidney (MDCK, ATCC number PTA-6500) cells were cultured in Dulbecco's minimal essential medium (DMEM, Cellgro) plus 10% fetal bovine serum (FBS). Mouse-adapted influenza A/PR/8/34 (H1N1) and A/Philippines/2/82/X-79 (H3N2) viruses were prepared as described in Quan et al., J Virol 2007; 81(7):3514-24, hereby incorporated by reference. The LD50 (lethal dose inducing 50% mortality) of these strains was determined by infection of mice with serial virus dilutions. RAW264.7 (ATCC number TIB-71) cells were cultured in DMEM plus 10% FBS.

Construction of a Membrane-Anchored Flagellin Gene

A full-length membrane-anchored flagellin encoding gene was generated by fusing encoding sequences of a signal peptide (SP) from honeybee mellitin Mellitin MKFLVN-VALVFMVVYISYIY ADPINMTGS (SEQ ID NO:26) and the transmembrane (TM) and cytoplasmic tail (CT) regions from the influenza A virus PR8 hemagglutinin (HA) to the 5' and 3' termini of the flagellin gene in frame, respectively. Influenza virus HA TM is DWILWISFAISCFLLCVALLG-FIMWAC (SEQ ID NO:24) and the CT is QKGNIRCNICI (SEQ ID NO:25). The substitution of the HIV Env signal peptide (SP) with that from honeybee mellitin was shown to promote higher-level expression and secretion of HIV-1 gp120 in insect cells. Substitution of the HIV TM-CT with sequences derived from the mouse mammary tumor virus (MMTV) envelope glycoprotein, influenza virus hemagglutinin, or baculovirus (BV) gp64 was found to enhance Env incorporation into VLPs.

The mellitin SP-encoding fragment was PCR amplified from the plasmid M-TM.CT$_{MMTV}$ as described in Wang et al., J. Virol., 2007, 81:10869-10878, hereby incorporated by reference, by use of primers 5'-GGTTCTAGAATGAAAT-TCTTAGTC-3'(SEQ ID NO:2) and 5'-GTGGGATC-CTTTCATGTTGATCGG-3' (SEQ ID NO:3) (XbaI and BamHI sites) and cloned into cloning vector pBluescript (−) with XbaI/BamHI sites, resulting in plasmid pBluescript-SP. The Salmonella enterica serovar Typhimurium flagellin gene (fliC; GenBank accession no. D13689) was amplified from plasmid pEM045 pEF6 FliC stop (a kind gift from Alan Aderem, Institute of Systems Biology, Seattle, Wash.) by using primers 5'-GCAGGATCCATGGCACAAGTCAT-3' (SEQ ID NO:4) and 5'-CGCGAATTCACGCAGTAAAGA-GAG-3' (SEQ ID NO:5) and inserted into pBluescript-SP, resulting in pBluescript-SP-FliC. HA TM-CT was amplified from plasmid pc/pS1 containing the full-length HA gene by using primers 5'-GCTAGAATTCCAGATTCTGGCGATC-3' (SEQ ID NO:6) and 5'-GCTAGGGCCCTTATCAGATG-CATATTCT-3' (SEQ ID NO:7) and cloned into pBluescript-SP-FliC to produce pBluescript-SP-FliC-HA tail. The full-length membrane-anchored flagellin gene was amplified from pBluescript-SP-FliC-HA tail by using primers 5'-GCTCGTCGACATGAAATTCTTAG-3'(SEQ ID NO:8) and 5'-GCTACTCGAGTTATCAGATGCATATTC-3' (SEQ ID NO:9) and cloned into pFastBac 1 under the control of the polyhedrin promoter. The sequence of the membrane-anchored flagellin gene was verified by DNA sequencing.

Construction of Genes Encoding 4 Repeats of M2e (4.M2e) and Fusion Proteins Containing 4.M2e Four DNA fragments encoding individual repeats of a consensus M2e (SLLTEVETPIRNEWGSRSNDSSDP) (SEQ ID NO: 1) and flexible linker sequences (AAA SLLTEVETPIRNEWGSRSNDSSDPAAGTSAAA SLLTEVETPIRNEWGSRSNDSSDPAAALQAAA SLLTEVETPIRNEWGSRSNDSSDPAAAACAAA SLLTEVETPIRNEWGSRSNDSSDPAAAACKL) (SEQ ID NO: 11) were produced by primer-extension PCR, and ligated together to generate the gene encoding 4.M2e. M2e contains two cysteine residues SLLTEVETPIRNEWGC RC NDSSDP (SEQ ID NO: 10) at sites 17 and 19. Since these cysteines could result in formation of intramolecular disulfide bonds and aggregation of particles under oxidative conditions, the two cysteine residues in M2e were replaced by two serine residues. To generate genes encoding fusion protein in which the variable region of FliC is replaced by 4.M2e, the DNA fragment encoding the variable region (AA 177-401 in FliC) was deleted from FliC gene (fliC, GenBank accession no. D13689, a gift from Dr. Alan Aderem), and replaced by the 4.M2e coding sequence by overlapping PCR. An N-terminal mellitin signal peptide (SP) and a C-terminal histidine (His) tag encoding sequences were added to the above fusion constructs in frame for protein production and purification. In addition, a membrane-anchored form of the 4.M2e-FliC construct was generated by adding the influenza HA (A/PR8) membrane-anchor coding sequence to the 4.M2e-FliC encoding gene in frame at the C-terminus as disclosed in Wang et al, J Virol, 2008, 82(23):11813-23 hereby incorporated by reference. The integrity of constructs was confirmed by DNA sequencing.

DNA sequence of the truncated flagellin with an HA transmembrane/cytoplasmic domains. TGAAATTCT-TAGTCAACGTTGCCCTTGTTTTTATGGTCGTGTA-CATTT CTTACATCTATGCGGACCCGATCAACAT-GACCGGATCCATGGCACAAGTCATT
AATACAAACAGCCTGTCGCTGTTGACCCA-GAATAACCTGAACAAATCCCAGTC
CGCTCTGGGCACCGCTATCGAGCGTCTGTCTTCCG-GTCTGCGTATCAACAGCG CGAAAGACGATGCG-GCAGGTCAGGCGATTGCTAACCGTTTTACCGC-GAACATC
AAAGGTCTGACTCAGGCTTCCCGTAACGCTAAC-GACGGTATCTCCATTGCGCA GACCACT-GAAGGCGCGCTGAACGAAATCAACAACAACCT-GCAGCGTGTGCGT
GAACTGGCGGTTCAGTCTGCTAACAGCAC-CAACTCCCAGTCTGACCTCGACTC CATCCAGGCT-GAAATCACCCAGCGCCTGAACGAAATCGACCGTG-TATCCGGCC
AGACTCAGTTCAACGGCGTGAAAGTCCTGGCGCA-GGACAACACCCTGACCAT CCAGGTTGGTGCCAAC-GACGGTGAAACTATCGATATCGATCTGAAGCA-GATCA
ACTCTCAGACCCTGGGTCTGGATACGCTGAAT-GTGGGCGCGCCGGTCTACCCG TATGACGTGCCG-GACTACGCGTCGCCATGGACAACCACCGAAAAC-CCGCTGC
AGAAAATTGATGCTGCTTTGGCACAGGTT-GACACGTTACGTTCTGACCTGGGT GCGGTACA- GAACCGTTTCAACTCCGCTATTACCAAC-
CTGGGCAACACCGTAAA
CAACCTGACTTCTGCCCGTAGCCGTATCGAAGAT-
TCCGACTACGCGACCGAAG TTTCCAACAT-
GTCTCGCGCGCAGATTCTGCAGCAGGCCGGTAC-
CTCCGTTCTG
GCGCAGGCGAACCAGGTTCCGCAAAACGTC-
CTCTCTTTACTGCGTGAATTCGG AGTGAAATTG-
GAATCAATGGGGATCTATCAGATTCTGGCGATC-
TACTCAACTG
TCGCCAGTTCACTGGTGCTTTTGGTCTC-
CCTGGGGGCAATCAGTTTCTGGATGT GTTCTAATG-
GATCTTTGCAGTGCAGAATATGCATCTGATAA (SEQ ID NO: 27)

Protein sequence of the truncated flagellin with the HA transmembrane/cytoplasmic domains.

MKFLVNVALVFMVVYISYIYADPINMTGS-
MAQVINTNSLSLLTQNNLNKS QSALGTAIERLSSGL-
RINSAKDDAAGQAIANRFTANIKGLTQASRNANDGI-
SIAQTT
EGALNEINNNLQRVRELAVQSANSTNSQSDLD-
SIQAEITQRLNEIDRVSGQTQFNG VKVLAQDNTL-
TIQVGANDGETIDIDLKQINSQTLGLDTLNVGAPVY-
PYDVPDYAS
PWTTTENPLQKIDAALAQVDTLRSDLGAVQNRFN-
SAITNLGNTVNNLTSARSRIE DSDYATEVSNMSRAQ-
ILQQAGTSVLAQANQVPQNVLSLLREF-
GVKLESMGIYQIL
AIYSTVASSLVLLVSLGAISFWMCSNGSLQCRICI (SEQ ID NO: 28)

Protein Purification

The above genes were cloned into the transfer vector pFastBac-1 (Invitrogen) and used for generating recombinant baculoviruses (rBVs) using the Bac-to-Bac insect cell protein expression system (Invitrogen) according to the manufacturer's instructions. His-tagged 4.M2e and 4.M2e-tFliC were purified using nickel affinity chromatography (Qiagen) by following the manufacturer's instructions. Sf9 cell cultures that were infected with rBVs expressing the above proteins were cleared by centrifugation (8000 rpm, 20 min). Proteins were purified from supernatants, dialyzed against PBS and stored at −80° C.

Flagellin VLP Production

A recombinant BV expressing the membrane-anchored 4.M2e-tFliC was generated as described above. Recombinant BVs expressing membrane-anchored FliC and M1 were described in Wang et al., J Virol, 2008, 82(23):11813-23, hereby incorporated by reference. The 4.M2e-FliC VLPs were produced by co-infection of sf9 cells with rBVs expressing the membrane-anchored 4.M2e-FliC and M1 at multiplicities of infection (MOIs) 6 and 3 respectively. The M2e content in 4.M2e-tFliC VLPs was 1.5% when normalized by western blot using purified 4.M2e as a standard. FliC VLPs were produced by co-infection of sf9 cells with rBVs expressing FliC and M1 with MOIs 6 and 3. VLPs were concentrated from the supernatants of Sf9 cell culture 60 h post-infection by porous fiber filtration using the Quixstand Benchtop system (GE Healthcare, Uppsala, Sweden) followed by sucrose density gradient ultracentrafugation. VLPs were characterized by protein assay, Western blot, sterility assay and electron microscopy (EM). VLPs were negatively stained for EM observation.

TLR-5-Specific Bioactivity Assay

The TLR5 binding activity of the above fusion protein and VLPs containing FliC were evaluated using a RAW264.7 cell-based assay. Soluble FliC was used as a positive control. VLPs containing M1 only were used as a negative control. All proteins or VLPs were diluted from 10 µg/ml to 0.001 ng/ml in 10-fold steps with DMEM medium containing 10% FBS. Cell cultures were treated with these diluted protein or VLP solutions. After 24 h treatment, cell culture supernatants were collected. Levels of tumor necrosis factor alpha (TNF-α) production stimulated by the above fusion protein of VLPs in both TLR5-positive and -negative cell cultures were determined by ELISA using a TNF-α assay kit (eBioscience, San Diego, Calif.) according to the manufacturer's instruction. TLR5 bioactivity was presented as the level of TNF-α production in TLR5 positive cells subtracting that in TLR5 negative cells.

Immunization and Challenge

Groups of six inbred female BALB/c mice (from Charles River Laboratory) were immunized three times with fusion proteins or M2e VLPs at defined doses as shown in Table 1 by the intramuscular (i.m.) or intranasal (i.n.) routes at 4-week intervals. Serum samples were collected at one week before prime immunization as preimmune sera. Immune sera and lung lavage samples were collected at 4 weeks after the last immunization. Blood samples were collected by retro-orbital plexus puncture. For virus challenge, mice were lightly anesthetized by inhalation of isoflurane, and 5 LD50 of mouse-adapted PR8 or Philippines viruses in a volume of 25 µA PBS were administered into mouse nostrils. Mouse body weight and survival were monitored daily for 15 days. Groups of infected mice were sacrificed at day 4 postinfection to determine lung virus loads. Lung virus titers were determined.

Antibody Responses

Serum M2e-specific IgG endpoint titers were determined by ELISA. 96-well ELISA plates (Nunc Life Technologies) were coated with 100 µM2e peptide (17 amino acids, 2 to 18, SLLTEVETPIRNEWGCR (SEQ ID NO: 89), synthesized at the Emory University Biochemical Core Facility) in carbonate buffer (pH 9.4, 5 µg/ml) at 4° C. overnight. The serum samples were serially diluted in twofold steps. The highest dilution which gave an OD450 twice that of the naïve group without dilution was designated as the antibody endpoint titer. Serum M2-specific antibody levels were determined using cell surface ELISA. MDCK cells in 96-well culture plates were grown near to 90% confluency and then infected with PR8 virus at a MOI of 1 ($5 \times 10^4$ pfu). After 12 h growth, the plates were washed and the cells were fixed with 0.5% glutaraldehyde at 4° C. for 30 min. After three washes with PBS, serial dilutions of test sera were added to the wells and incubated for 2 h in room temperature. Antibody binding to non-infected MDCK cells was subtracted as a background. M2-specific antibody levels were presented as the value of OD450.

For the determination of mucosal antibody levels, lung lavages of immunized mice were evaluated for IgA and IgG endpoint titers as described above for serum IgG using HRP-conjugated rabbit anti-mouse IgA as the secondary antibody.

Purification of Fusion Proteins and Production of VLPs

M2e in repetitive forms is immunogenic. A fusion protein of 4.M2e attached to the C-terminal of the typhimurium phase II flagellin fljB was found to be quantitatively and qualitatively superior to M2e in inducing anti-M2 immunity. Huleatt et al., Potent immunogenicity and efficacy of a universal influenza vaccine candidate comprising a recombinant fusion protein linking influenza M2e to the TLR5 ligand flagellin. Vaccine 2008; 26(2):201-14. A DNA fragment was generated encoding a consensus M2e peptide (upper panel in FIG. 1). A histidine (His)-tagged fusion protein 4.M2e-tFliC (lower panel in FIG. 1) was also constructed in which the variable region of the FliC was replaced by 4.M2e, and the fusion protein was produced from sf9 cell cultures in a BV-based protein expression system. A his-tagged 4.M2e was also constructed and purified as a control.

Figure 2B:
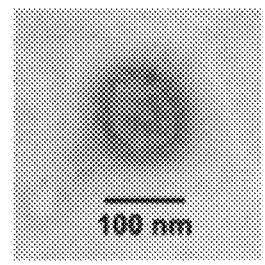
Figures 2C, 2D, 2E:
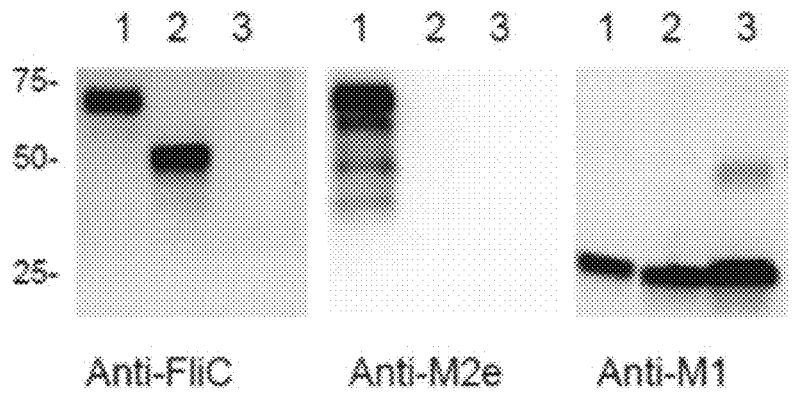

To further improve the immunogenicity of M2e, membrane-anchored fusion protein 4.M2e-tFliC gene (lower panel FIG. 1), was constructed and incorporated into influenza M1-derived VLPs as schematized in FIG. 2A. The integrity of VLPs was confirmed by electron microscopy (FIG. 2B). The incorporation of the membrane-anchored 4.M2e-tFliC in VLPs was confirmed by western blotting assays using either anti-FliC antibody (lane 1 in FIG. 2C) or anti-M2e antibody (14C2, lane 1 in FIG. 2D). FliC/M1 VLPs were produced as control. The incorporation of FliC into FliC/M1 VLPs was confirmed by western blot using anti-FliC (Lane 2 in FIG. 2C) or anti-M1 antibody (FIG. 2E).

Figure 2F:
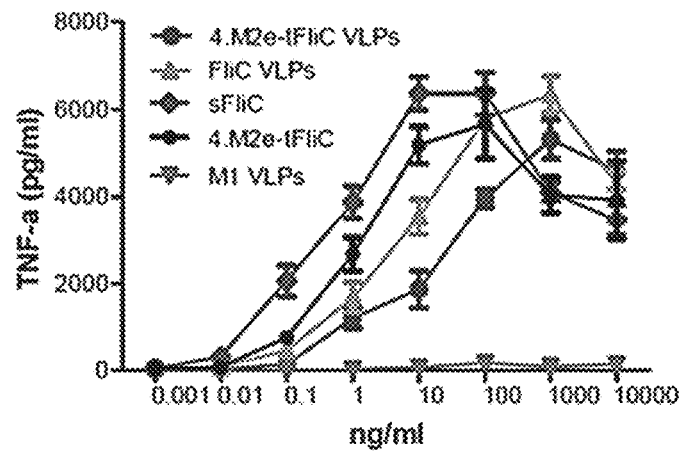

Because TLR5 is the extracellular sensor of flagellin, the ability of the soluble M2e-tFliC fusion protein, or the membrane-anchored fusion protein in VLPs, to function as a TLR5 ligand was determined. As shown in FIG. 2F, either the fusion protein or VLPs containing FliC showed TLR5-specific bioactivity, inducing a mouse macrophage cell line RAW264.7 to produce TNF-α in a concentration range of 0.01 ng to 1000 ng/ml. The 50% effective concentration (concentration which produces 50% of maximal activity, EC50) of 4.M2e-tFliC was 5 ng, and that of the 4.M2e-tFliC VLPs was 60 ng. The $EC_{50}$ of the soluble flagellin was 0.8 ng/ml. Considering that the soluble FliC has a much lower molecular weight than the fusion protein or VLPs, $EC_{50}$ titers are within expected ranges.

The 4.M2e-tFliC Fusion Protein or VLPs Induce High IgG Responses

Figure 3A:
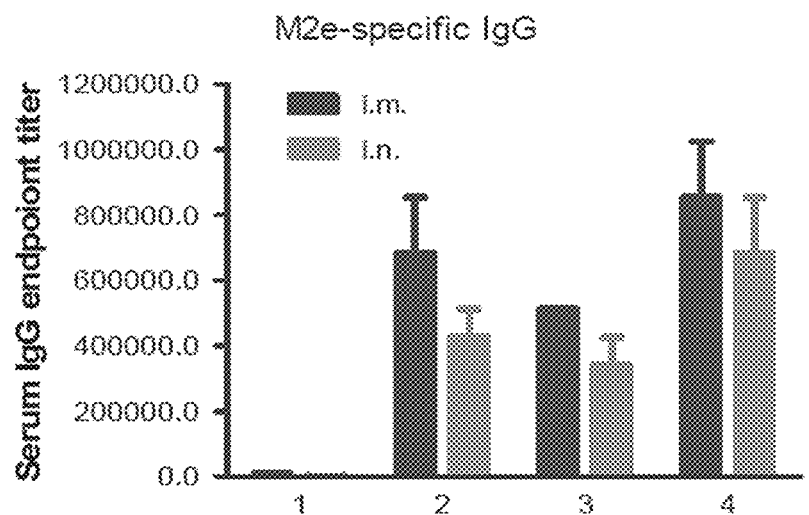

To evaluate the potential of multiple M2e-containing fusion protein or VLPs as universal influenza vaccines, mouse groups (6 mice in each group) were immunized three times at 4-week intervals with doses indicated in Table 1. The immune responses were compared by either intramuscular (i.m.) or intranasal (i.n.) immunization. The result in FIG. 3A showed that both the fusion protein and VLP groups trigger robust humoral responses against M2e by either the i.m. or i.n. route compared to the 4.M2e group which showed a very low serum IgG response. The serum IgG titers in i.m. and i.n. immunizations were $6.5 \times 10^5$ and $4.0 \times 10^5$, respectively. An interesting observation is that soluble 4.M2e protein when adjuvanted with flagellin VLPs induced higher levels of serum IgG titers ($8.2 \times 10^5$ for i.m, $6.4 \times 10^5$ for i.n, geometric mean), demonstrating the adjuvant effect of FliC in a particulate form.

TABLE 1

Mouse groups for immunization.

| Group | Antigen form | Dose (µg) | Number of immunization | Immunization route |
|---|---|---|---|---|
| 4.M2e | Protein | 10 | 3 | i.m. |
| 4.M2e | Protein | 10 | 3 | i.n. |
| 4.M2e-tFliC | Fusion protein | 10 | 3 | i.m. |
| 4.M2e-tFliC | Fusion protein | 10 | 3 | i.n. |
| 4.M2e-tFliC VLPs | VLPs | 50 | 3 | i.m. |
| 4.M2e-tFliC VLPs | VLPs | 50 | 3 | i.n. |
| 4.M2e + tFliC VLPs | Mixture | 10 + 10 | 3 | i.m. |
| 4.M2e + tFliC VLPs | Mixture | 10 + 10 | 3 | i.n. |
| Naïve mice | | | | | i.m., intramuscular; i.n., intranasal.

Three immunizations were performed at 4 weeks intervals.

Figure 3B:
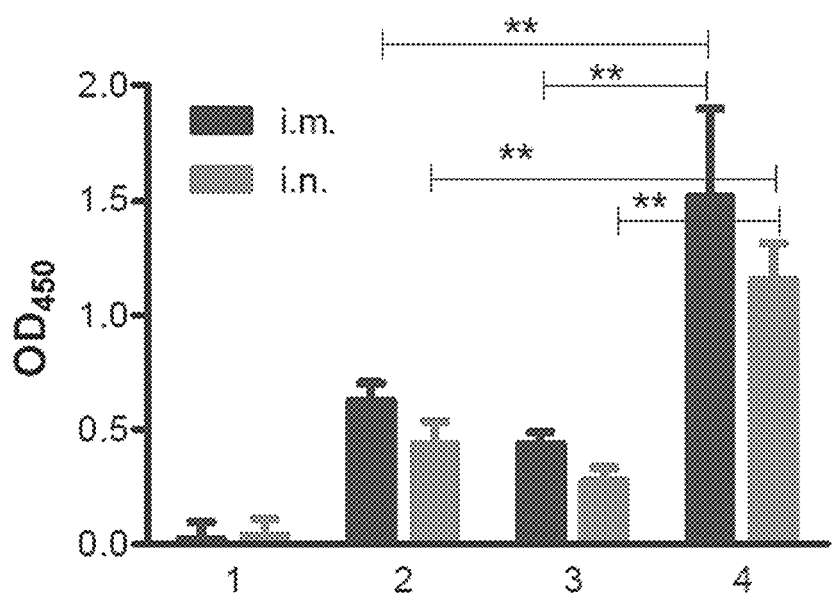

Although the 4.M2e-tFliC fusion protein or its membrane-anchored form in VLPs induced a high level of M2e-specific antibody responses, only antibodies capable of targeting native tetrameric M2 may confer protection. Influenza virus-infected MDCK cells express high levels of M2 on the cell membrane and can be used to determine the M2-specific antibody binding. Therefore antibodies binding to native M2 protein were evaluated by a MDCK cell-based ELISA. As shown in FIG. 3B, antibodies in immune sera recognized and bound M2 expressed on MDCK cell surfaces in ELISA. Sera from the 4.M2e peptide-immunized mice showed very low binding close to background. The mixture of 4.M2e plus FliC VLPs induced highest M2-specific antibody responses.

Comparatively, the i.m. immunization induced better systemic immune responses than the i.n. route. The antibody-binding levels to M2 on cell surface in all groups showed similarity with M2e-specific IgG titers, demonstrating that the M2e-specific antibodies confer M2 recognition and are correlated with binding to the native M2.

The 4.M2e-tFliC Fusion Protein or VLPs Induce Enhanced Mucosal Immune Responses

Figure 4A:
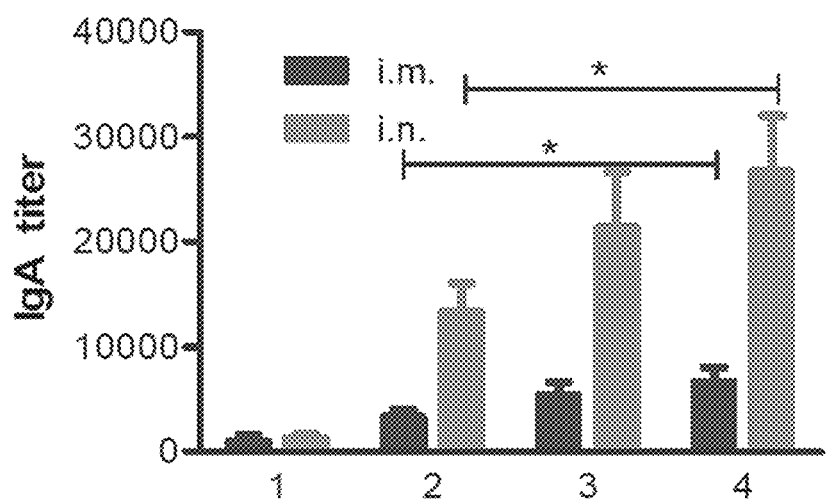
Figure 4B:
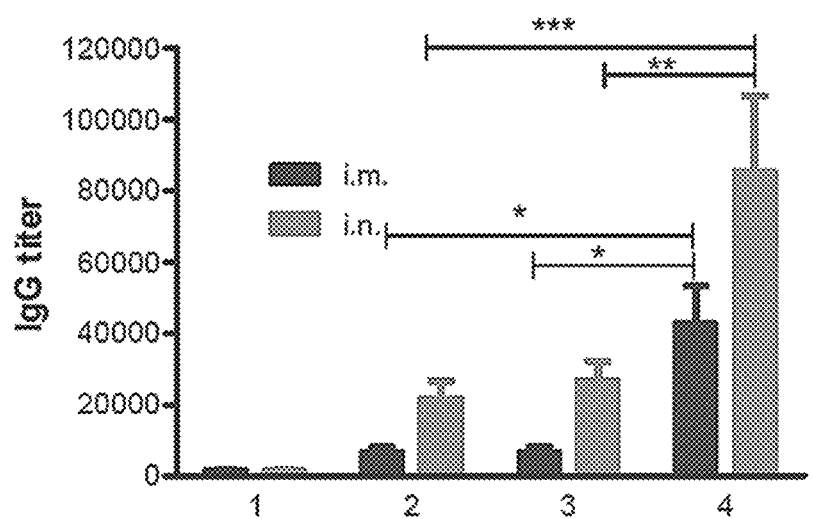

The respiratory tract is the dominant site of influenza virus infection and replication. Effective mucosal antibody responses can prevent the initiation of viral infection in the respiratory tract. FliC with the deletion of the variable region has been reported to be an effective mucosal adjuvant. Nempont et al., J Immunol, 2008, 181(3):2036-43. The result in FIG. 4 shows that both the 4.M2e-tFliC fusion protein and VLPs induced higher titers of secretory IgA (sIgA, FIG. 4A) and IgG (FIG. 4B) in respiratory secretions after i.n. immunization. Data also demonstrate that flagellin-containing VLPs are very effective as a mucosal adjuvant when mixed with 4.M2e, inducing high titers of sIgA ($3.2 \times 10^4$) and IgG ($8 \times 10^4$) responses at mucosal surfaces. These data demonstrate that flagellin is effective as a mucosal adjuvant when associated with M2e antigen in fusion proteins or VLPs, or mixtures of M2e and FliC VLPs.

The Breadth of Protective Efficacy of 4.M2e-tFliC Fusion Proteins or VLPs

Figure 5A:
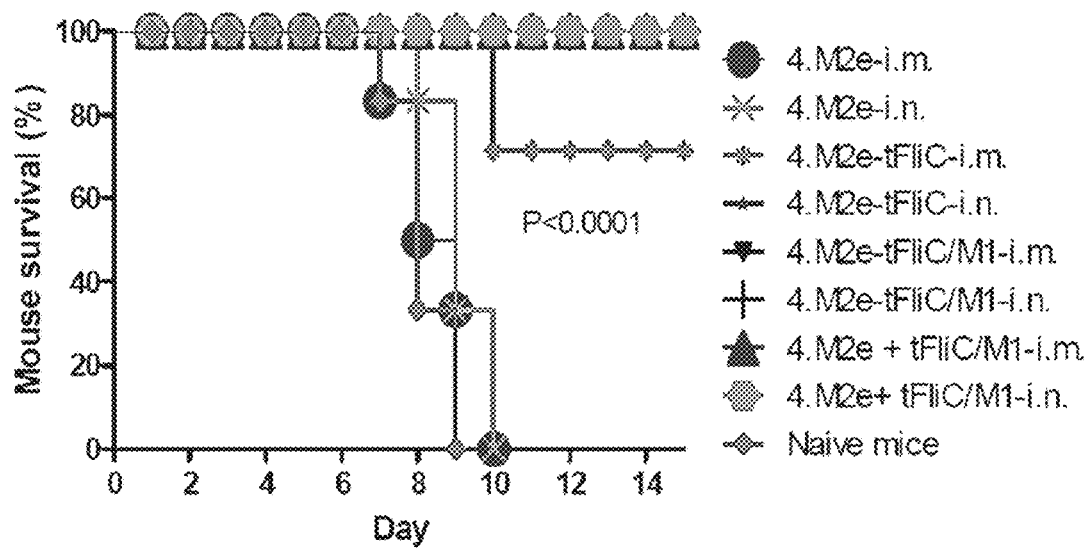
Figure 5B:
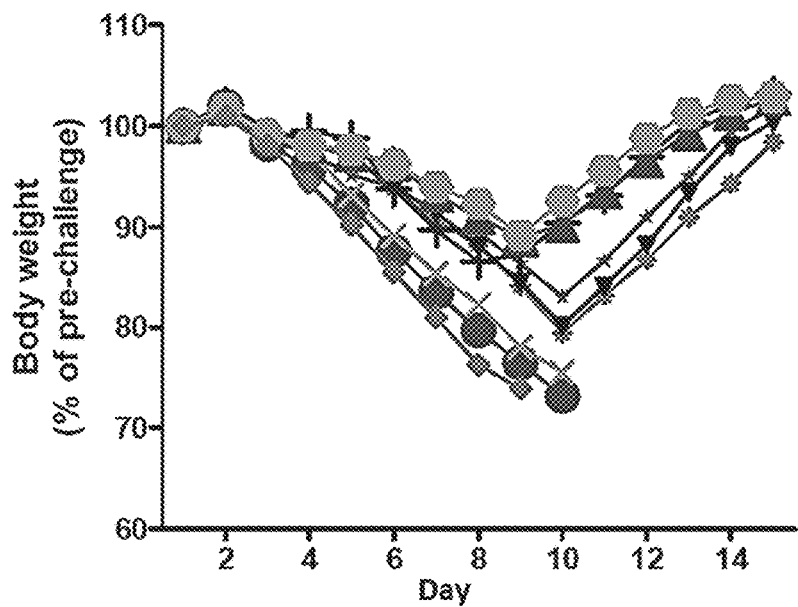

The above results demonstrate that the immunogenicity of M2e is enhanced by insertion of 4.M2e into FliC to replace the variable region, or by assembly of the membrane-anchored 4.M2e-tFliC into VLPs. To determine whether the above vaccine candidates confer enhanced protection to influenza virus challenge, immunized mice were challenged i.n. with 5 LD50 (250 pfu) of mouse-adapted A/Philippines (H3N2) virus in which the M2e has the same sequence as the consensus used for making the fusion protein or VLPs (FIG. 1). Also, this sequence is the one most frequently found in human influenza virus strains. As shown in FIG. 5, five groups (i.n.-delivered 4.M2e-tFliC fusion protein, both i.m. and i.n.-delivered 4.M2e-tFliC VLPs, and mixtures of 4.M2e plus FliC VLPs) of immunized mice completely survived the Philippines virus challenges (FIG. 5A). Mice immunized with mixtures of 4.M2e and FliC VLPs lost less bodyweight (8 and 10% for i.n. and i.m. immunizations, respectively. FIG. 5B), revealing the best comparative protection. Mice immunized i.n. with 4.M2e-tFliC VLPs and 4.M2e-FliC fusion protein lost their 12 and 17% of bodyweight, respectively (FIG. 5B). Mice immunized i.m. with 4.M2e-tFliC fusion protein survived 67% (4 of 6 mice, FIG. 6A) in the challenge with a 20-25% body weight loss (FIG. 5B). Mice immunized either i.n. or i.m. with 4.M2e protein, as well as the naïve mice, reached their endpoints (FIGS. 5A and B).

Figure 6A:
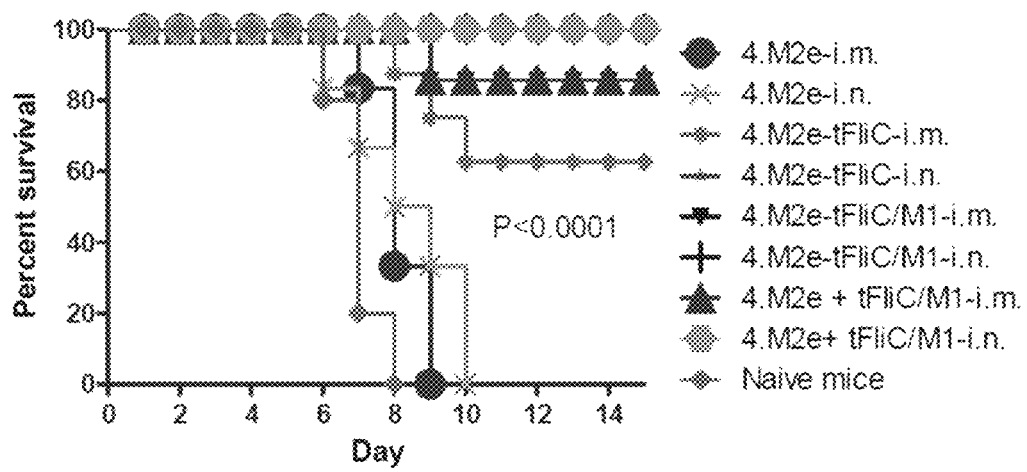

The protection induced by the 4.M2e-tFliC fusion protein or VLPs against A/PR8 virus challenge were further evaluated. The M2e sequence of PR8 M2 that were used in this work has one amino acid difference from the consensus, and no other human influenza virus shares this M2e sequence. Four weeks after the last immunization, mice were infected i.n. with a dose of 5 LD50 (125 pfu) of mouse-adapted PR8 live virus. Intranasally-immunized mice showed complete protection against PR8 challenge (FIG. 6A). Some i.m.-immunized mice survived except for the mixture of the 4.M2e peptide plus FliC VLPs (FIG. 6A), which induced full protection by either i.n. or i.m. immunization.

Figure 6B:
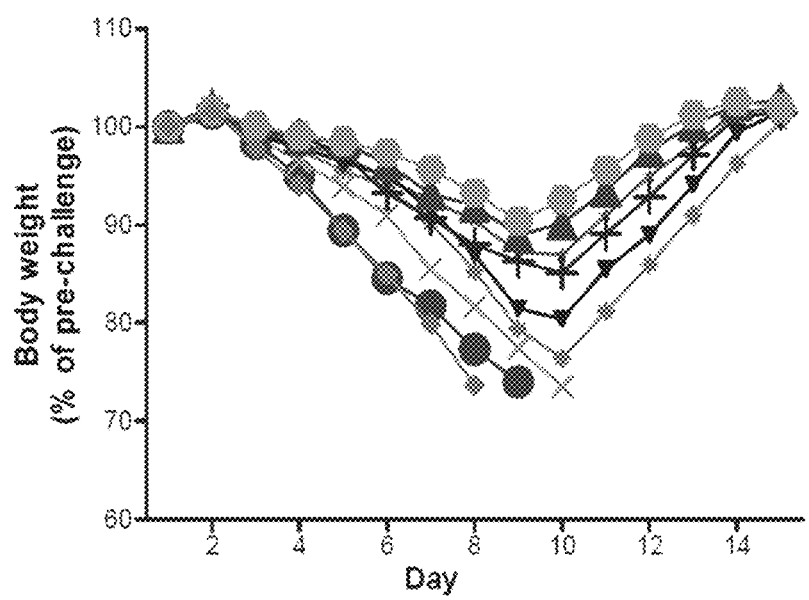

A common feature of the above challenge results is that i.n. immunity is much more effective in providing protection against influenza virus infection. As shown in FIG. 5, i.n and i.m.-delivered 4.M2e-tFliC fusion proteins induced 100 and 67% (4 of 6 mice) protection against Philippines virus challenges, respectively. I.n.-immunized mice with 4.M2e-tFliC VLPs survived both Philippines and PR8 challenges, but 17% (1 of 6) of i.m. immunized mice were terminated after PR8 challenge (FIG. 6A). Although mice immunized both i.m. and i.n. by the mixture of 4.M2e and FliC VLPs survived 100% in either Philippines or PR8 virus challenge, respectively, i.n.-immunized mice lost less body weight, as shown in FIGS. 5B and 6B. In all the above immunized mice, i.m. immunizations induced higher titers of serum M2-specific IgG responses compared to i.n immunizations as shown in FIG. 3, but the i.n. vaccination induced better protection, demonstrating the advantage of mucosal immunity in M2e-induced protective immunity.

Figure 7:
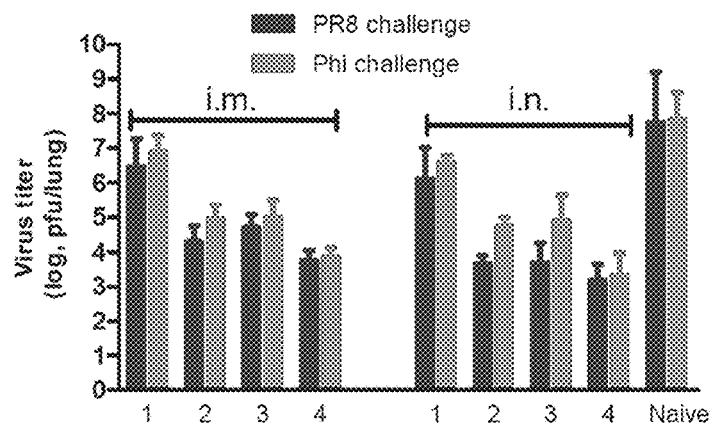

Because the M2e-specific antibodies do not neutralize the infectivity of influenza viruses but instead exert their protective effect at the level of the infected cell, the effect of 4.M2e-tFliC or VLPs in decreasing the viral replication in mouse lung was further evaluated. As shown in FIG. 7, all surviving groups have lung virus loads lower than $1\times10^4$ for the PR8 challenge, or $1\times10^5$ for Philippines. The i.n.-immunized mice showed lower lung virus titers than i.m. groups, further demonstrating the advantage of mucosal immunization.

Construction of rBVs Expressing RSV F, RSV G, and Influenza M1

Figure 8A:
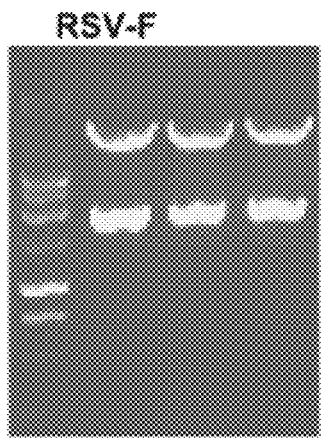
Figure 8B:
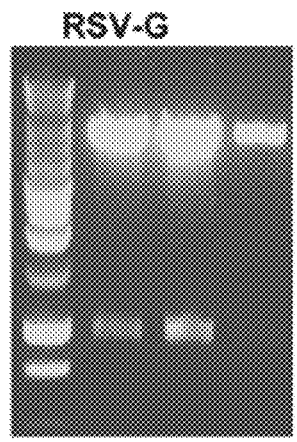
Figure 8C:
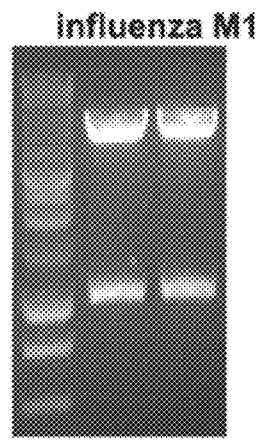

RSV-F and RSV-G genes from RSV strain A2 were amplified by PCR, and the influenza M1 gene was amplified by RT-PCR with primers containing restriction enzyme sites. Genes were cloned into pFastBac vectors, and insertion of RSV-F, RSV-G, and influenza M1 in pFastBac expressing vectors was confirmed by cutting with enzyme sites, EcoRI and XhoI (FIG. 8A-C). The nucleotide sequences of the RSV-F, RSV-G, and influenza M1 genes were found to be identical to the previously published sequences (accession numbers FJ614814 for F, AF035006 for G, FJ966085 for M1, all hereby incorporated by reference) by DNA sequencing The RSV A2 F and G genes were polymerase chain reaction (PCR)-amplified using RNA from infected HEp-2 cells as described in Moore et al. A chimeric A2 strain of respiratory syncytial virus (RSV) with the fusion protein of RSV strain line 19 exhibits enhanced viral load, mucus, and airway dysfunction, J Virol, 2009, 83:4185-94, hereby incorporated by reference. The RSF-F gene was PCR-amplified from a complementary DNA (cDNA) clone of A2 F by use of primers 5-AAA GAATTCACCATGGAGGAGTTGCTAATCCTCAA-3 (SEQ ID NO: 82) and 5-TTA CTCGAGTTAGTTACTAAATGCAATATTATT-3 (SEQ ID NO: 83) (EcoRI and XhoI underlined) and cloned into pFastBac with EcoRI/XhoI sites, resulting in plasmid pFastBac-F. The RSV-G gene was PCR-amplified from a cDNA clone of A2 G by use of primers 5-AAA GAATTCACCATGTCCAAAAACAAGGACCAAC-3 (SEQ ID NO: 84) and 5-TTA CTCGAGTACTGGCGTGGTGTGTTG-3 (SEQ ID NO: 85) (EcoRI and XhoI underlined) and cloned into pFastBac with EcoRI/XhoI sites, resulting in plasmid pFastBac-G.

For influenza M1 gene cloning, A/California/04/2009 virus was inoculated into MDCK cells and total viral RNA was extracted using an RNeasy Mini kit (Qiagen). Reverse transcription (RT) and PCR were performed on extracted viral RNA using the One-Step RT-PCR system (Invitrogen) with gene-specific oligonucleotide primers. The following primer pairs were used for M1: 5-AAA GAATTCACCATGAGTCTTCTAACCGAGGT-3 (SEQ ID NO: 86) and 5-TTA CTCGAGTTACTCTAGCTCTATGTTGAC-3 (SEQ ID NO: 87) (EcoRI and XhoI underlined). Following RT-PCR, a cDNA fragment containing the M1 gene was cloned into the pFastBac vector.

Recombinant baculoviruses (rBVs) expressing RSV F, RSV G, or influenza M1 were generated. Transfections of DNA containing the above genes were accomplished using cellfectin II (Invitrogen) with SF9 cells as recommended by the manufacturer, followed by transformation of pFastBac containing RSV-F or RSV-G or M1 with white/blue screening. The rBVs were derived by using a Bac-to-Bac expression system (Invitrogen) according to the instructions of the manufacturer.

Production of RSV VLPs

RSV-F VLPs were produced by infecting Sf9 cells with rBVs expressing RSV-F and M1. RSV-G VLPs were produced by infecting Sf9 cells with rBVs expressing RSV-G and M1. Cell culture supernatants were collected on day 2 postinfection with centrifugation at 6000 rpm for 20 minutes at 4 C. VLPs were concentrated with QuixStand (GE) and purified through a 20%-30%-60% discontinuous sucrose gradient at 30 000 rpm for 1 hour. The VLP bands between 30% and 60% were collected and then diluted with phosphate-buffered saline (PBS) and pelleted at 28 000 rpm for 40 minutes at 4 C. VLPs were resuspended in PBS overnight at 4 C.

Figure 8D:
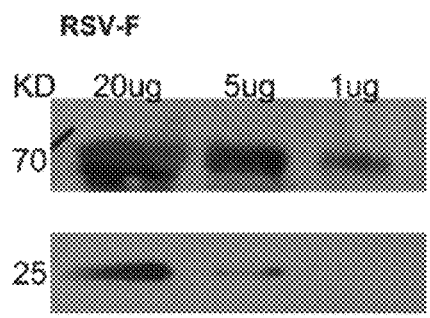
Figure 8E:
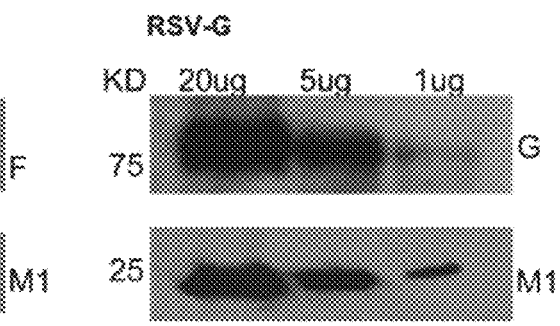

The incorporation of F or G and M1 into VLPs was confirmed by western blot using anti-RSV or anti M1 polyclonal antibodies (FIGS. 8D and E). Both RSV-F or RSV-G VLPs showed spherical shapes with spikes on their surfaces (FIGS. 9A and C). RSV F VLPs had a peak in size distribution at 80-100 nm, whereas G-VLPs were similar but somewhat more heterogeneous in size (FIGS. 9B and D). In total, 5-7.5 mg VLPs/liter of cell culture medium were obtained, and their antigenic properties were stable for 1 year at −80 C. Heat-treated VLPs lost immunogenicity and protective capacity.

Antibody Responses in Immune Serum

Figure 10B:
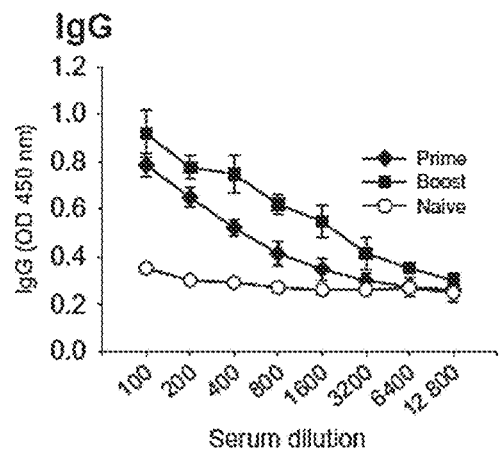
Figure 10C:
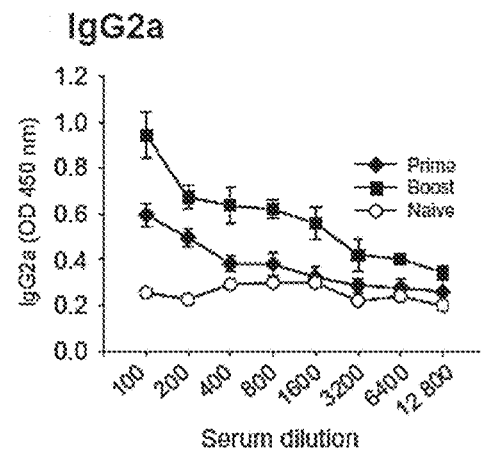
Figure 10D:
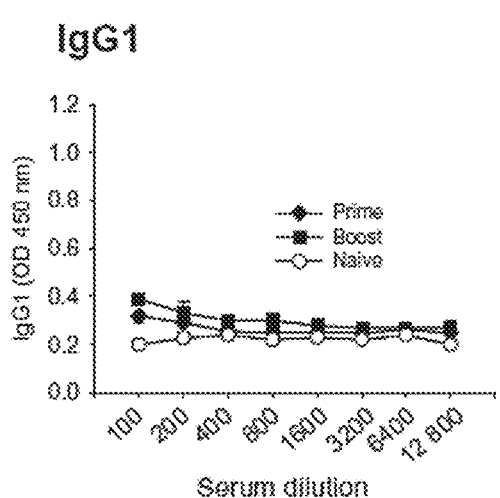
Figure 10E:
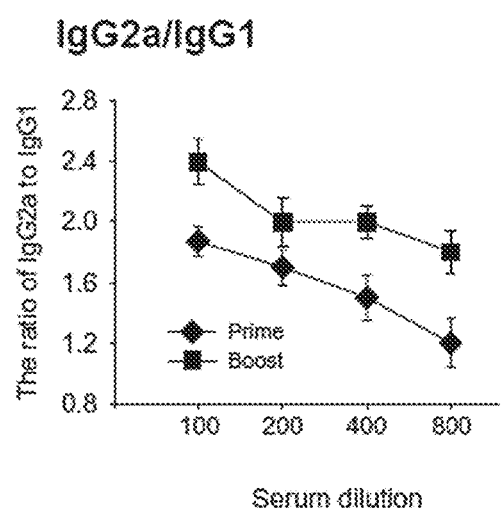
Figure 10F:
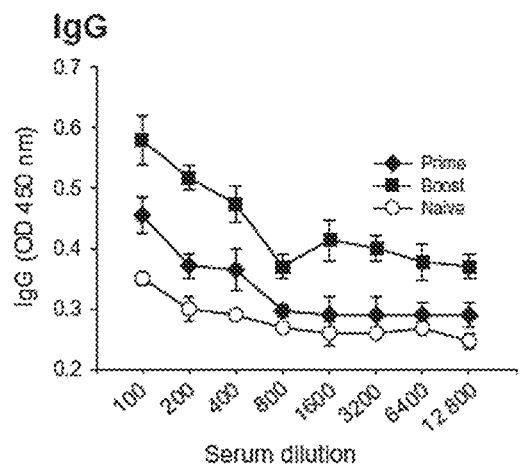
Figure 10G:
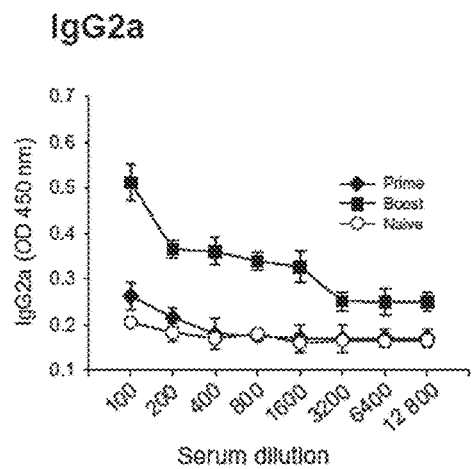
Figure 10H:
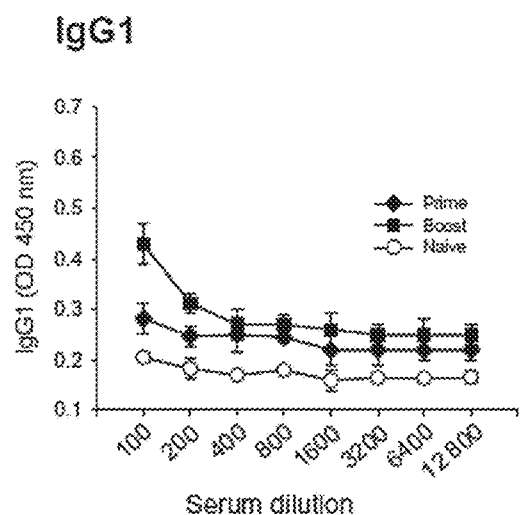
Figure 10I:
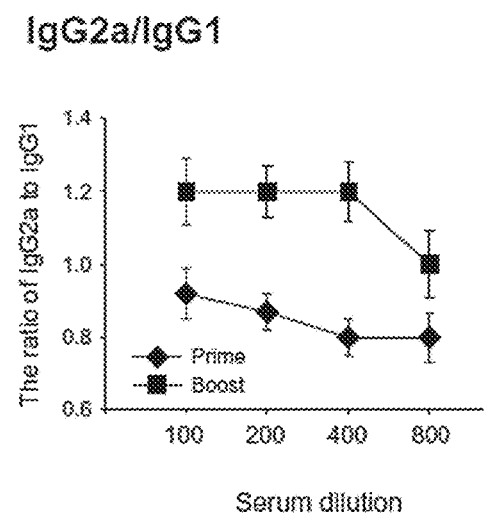

Serum antibody responses were determined in mice immunized with RSV-F or RSV-G VLPs as shown in FIG. 10A. The levels of total IgG, IgG2a, and IgG1 antibody responses in the serum specific to RSV after prime and boost were determined. Total IgG and IgG2a responses from the mice immunized with RSV-F VLPs showed significantly higher titers after boost compared with those after prime, indicating the progressive maturation of virus-specific antibodies (FIGS. 10B and C). Low IgG1 responses were observed both after prime and boost (FIG. 10D). In contrast, the levels of IgG2a antibody increased significantly, both after prime and boost, compared with IgG1. The levels of IgG2a were higher after boost than prime at various serum dilutions (FIG. 10E). Similar patterns of total IgG, IgG2a, and IgG1 responses to RSV A2 were found in mice immunized with RSV-G VLPs. The levels of IgG and IgG2a antibody responses were lower relative to those observed with RSV-F VLPs. Antibody responses (IgG, IgG2a) were significantly higher in mice after boost compared with primary immunization (FIGS. 10F and G). As seen in FIG. 10, IgG2a-dominant responses were found after the boost but not after prime. These results indicate that both RSV-F and RSV-G VLPs are highly immunogenic and induce IgG2a-dominant responses.

Antibody Responses in Mouse Lung

Figure 11A:
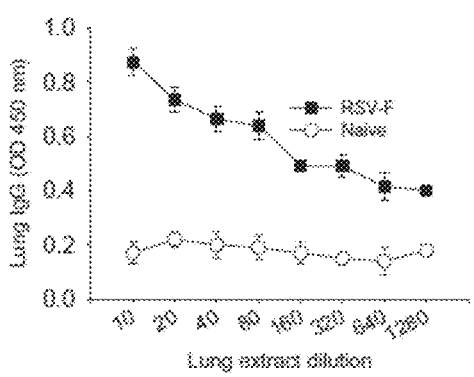
Figure 11B:
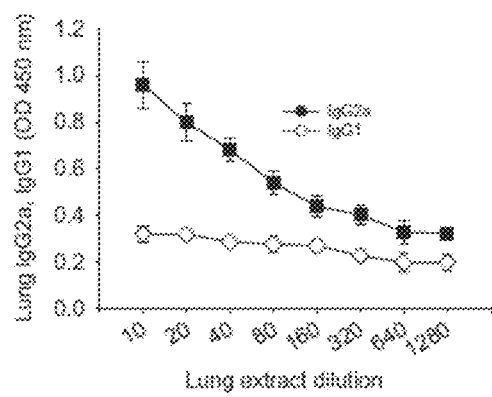
Figure 11C:
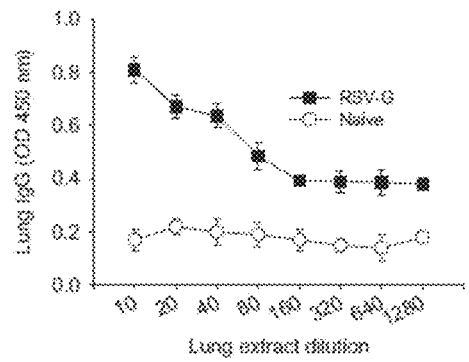
Figure 11D:
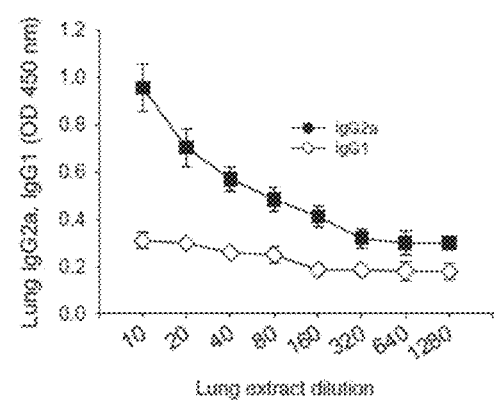
Figure 11E:
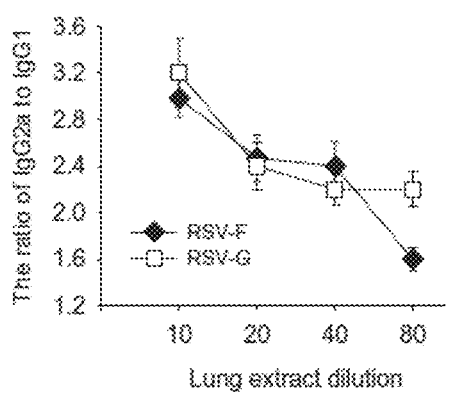

The lung is an important location for RSV replication, where disease development occurs. At day 4 after challenge, mouse lungs were harvested and total IgG, IgG1, and IgG2a antibody responses were determined. As shown in FIGS. 11A and C, significantly higher levels of RSV A2 specific IgG antibodies were found in mice immunized with RSV-F VLPs or RSV-G VLPs. Interestingly, IgG responses specific to RSV-G or RSV-F in immunized mice showed similarly high levels. As seen in FIGS. 11B and D, significantly higher IgG2a responses were elicited in mice immunized with RSV-F VLPs or RSV-G VLPs compared with IgG1. The ratios of IgG2a to IgG1 from both RSV-G VLPs and RSV-F VLPs were similar at lung extract dilutions of 10, 20, and 40 (FIG. 11E). Compared with serum samples, lung extract samples showed a much higher ratio of IgG2a to IgG1 (FIGS. 11E and I, FIG. 11E). These results indicate that both RSV-G VLPs and RSV-F VLPs elicit RSV IgG2a dominant responses in lungs.

Immune Sera Effectively Bind to RSV Infected Cells

Figure 12A:
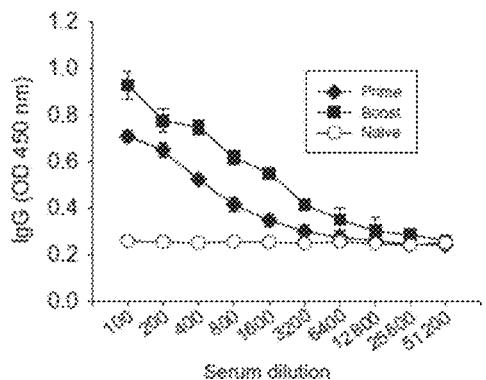
Figure 12B:
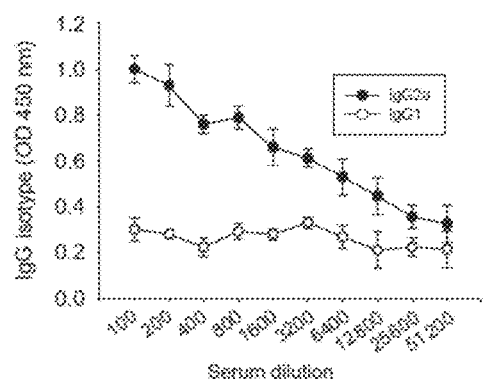
Figure 12C:
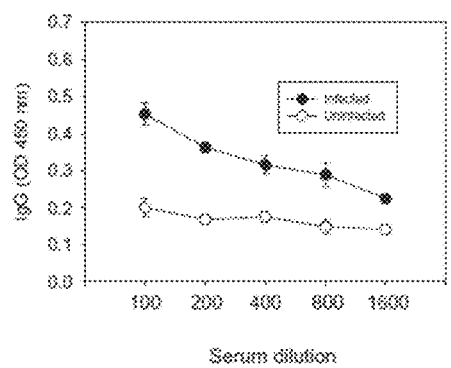
Figure 12D:
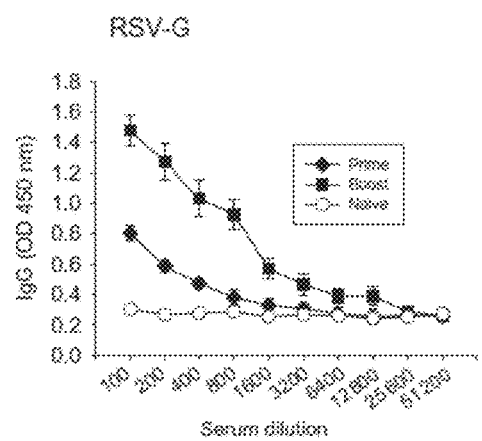
Figure 12E:
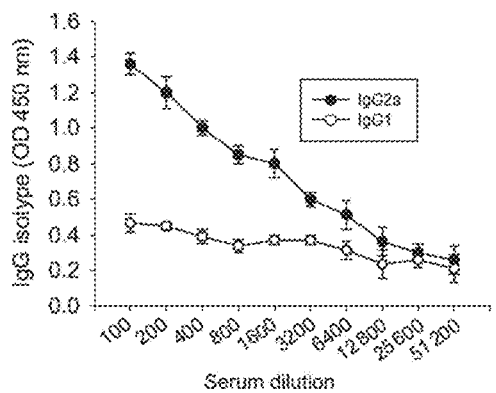
Figure 12F:
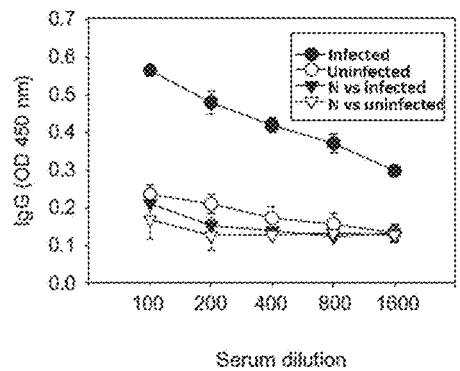

Immune responses against cell surface proteins were determined using monolayers of HEp-2 cells infected with RSV A2 or uninfected cells. After 12 hours of incubation, the supernatants were removed and the immune sera were added to the cell surface to determine IgG, IgG1 and IgG2a responses. As seen in FIG. 12, sera from mice immunized with RSV-F or RSV-G VLPs from prime and boost showed significantly high levels of total IgG and IgG2a antibody responses against cell surface proteins expressed 12 hours postinfection (FIGS. 12A, B, D, and E). Total IgG responses against infected or uninfected cell surface proteins were determined in mice immunized with RSV-F VLPs (FIG. 12C) or with RSV-G VLPs (FIG. 12F), showing background responses in uninfected cells. Interestingly, RSV-G VLP vaccinations showed much higher total IgG and IgG2a responses against cell surface proteins than did RSV-F VLPs. These results indicate that immune sera specifically bind to HEp-2 cell surface expressed proteins.

Neutralizing Antibody Responses

Neutralizing antibody is an important functional component of immune responses induced by vaccination. To determine whether immunization with RSV VLPs induces neutralizing antibodies, an in vitro plaque reduction assay was used. Serially diluted mouse sera at week 3 after boost were complement inactivated, incubated with live RSVA2, and plaque assays were conducted. As shown in FIG. 13, RSV-F or RSV-G VLPs showed similar plaque reduction rates. At 1:1000 serum dilutions, either RSV-G or RSV-F VLP vaccination reduced the number of plaques by 55% whereas naïve serum reduced plaques by 7%. At the 1:10 000 serum dilutions, RSV-G VLPs showed 38% plaque reduction versus 25% reduction by RSV-F VLPs and no reduction by naive sera (FIG. 13). Naive sera showed very high background effects at serum dilution of 1:10 or 1:100, with neutralizing titers 0.100. Virus neutralizing titers from immunization with RSV-F or RSV-G VLPs were 0.1000 when the highest serum dilution showing 50% plaque reduction was taken as the neutralizing antibody titer in comparison to the negative medium control showing no plaque reduction. These results indicate that RSV-F and RSV-G VLPs vaccines can induce protective functional antibodies to RSV.

Protection Against Live RSV A2 Virus Challenge Infection

Virus load in lungs and body weight changes following challenge infection are important indicators to assess vaccine protective efficacy. Immunized mice were challenge infected with live RSV-A2 virus ($1.5 \times 10^6$ PFU/mouse) at 4 weeks after boost, and lung virus loads at day 4 postchallenge were determined. As shown in FIG. 14A, significantly decreased lung virus loads were detected in mice immunized with RSV-F (11-fold) or RSV-G VLPs (600-fold) compared with naive mouse controls. The difference in lung virus loads in mice immunized with RSV-F VLPs and RSV-G VLPs also was compared (FIG. 14B). Lower lung virus load was found in mice immunized with RSV-G VLPs than those in mice immunized with RSV-F VLPs (FIG. 14B). These results indicate that vaccination of mice with RSV-F or RSV-G VLPs effectively can inhibit virus replication in lung. The level of body weight loss postchallenge was measured, and days 6 or 7 postinfection showed the highest body weight loss. Naive control mice showed the highest body weight loss (20%), whereas mice immunized with RSV-F VLPs or RSV-G VLPs showed 13% and 6.4% of body weight loss, respectively, at day 6, and 8% and 5% of body weight loss, respectively, at day 7 postchallenge (FIG. 14C). Significant differences in body weight loss were found at day 7 between naive controls and RSV-F or RSV-G VLPs, and between RSV-F and RSV-G VLPs. The differences correlate with better lung virus clearance, which was observed with RSV-G VLPs compared with RSV-F VLPs. These results indicate that RSV-F and RSV-G VLPs both confer substantial protection of mice from RSV-induced illness.

What we claim:

1. A method of vaccinating a subject comprising administering an antigen wherein the antigen consists of four copies of M2e polypeptide of SEQ ID NO: 1, in combination with a virus-like carrier comprising a flagellin in a membrane-anchored form comprising a polypeptide of SEQ ID NO: 28, wherein the virus-like carrier does not contain the antigen, under conditions such that antibodies to the antigen are produced.

2. The method of claim 1, wherein the antigen and virus-like carrier are administered intranasally or intramuscularly.

3. An immunogenic composition comprising an antigen wherein the antigen consists of four copies of M2e polypeptide of SEQ ID NO: 1 and a virus like carrier comprising a flagellin in a membrane-anchored form comprising a polypeptide of SEQ ID NO: 28 wherein the virus-like carrier does not contain the antigen.

* * * * *

SEQUENCE LISTING

<160> NUMBER OF SEQ ID NOS: 89

<210> SEQ ID NO 1

-continued

```
<211> LENGTH: 24
<212> TYPE: PRT
<213> ORGANISM: Salmonella enterica

<400> SEQUENCE: 1

Ser Leu Leu Thr Glu Val Glu Thr Pro Ile Arg Asn Glu Trp Gly Ser
1               5                   10                  15

Arg Ser Asn Asp Ser Ser Asp Pro
            20

<210> SEQ ID NO 2
<211> LENGTH: 24
<212> TYPE: DNA
<213> ORGANISM: Influenza A virus

<400> SEQUENCE: 2
ggttctagaa tgaaattctt agtc                                      24

<210> SEQ ID NO 3
<211> LENGTH: 24
<212> TYPE: DNA
<213> ORGANISM: Influenza A virus

<400> SEQUENCE: 3
gtgggatcct ttcatgttga tcgg                                      24

<210> SEQ ID NO 4
<211> LENGTH: 23
<212> TYPE: DNA
<213> ORGANISM: Salmonella enterica

<400> SEQUENCE: 4
gcaggatcca tggcacaagt cat                                       23

<210> SEQ ID NO 5
<211> LENGTH: 24
<212> TYPE: DNA
<213> ORGANISM: Salmonella enterica

<400> SEQUENCE: 5
cgcgaattca cgcagtaaag agag                                      24

<210> SEQ ID NO 6
<211> LENGTH: 25
<212> TYPE: DNA
<213> ORGANISM: Salmonella enterica

<400> SEQUENCE: 6
gctagaattc cagattctgg cgatc                                     25

<210> SEQ ID NO 7
<211> LENGTH: 28
<212> TYPE: DNA
<213> ORGANISM: Salmonella enterica

<400> SEQUENCE: 7
gctagggccc ttatcagatg catattct                                  28

<210> SEQ ID NO 8
<211> LENGTH: 23
<212> TYPE: DNA
<213> ORGANISM: Salmonella enterica

<400> SEQUENCE: 8
```

```
                                                   -continued gctcgtcgac atgaaattct tag                                             23

<210> SEQ ID NO 9
<211> LENGTH: 27
<212> TYPE: DNA
<213> ORGANISM: Salmonella enterica

<400> SEQUENCE: 9
gctactcgag ttatcagatg catattc                                         27

<210> SEQ ID NO 10
<211> LENGTH: 24
<212> TYPE: PRT
<213> ORGANISM: Salmonella enterica

<400> SEQUENCE: 10

Ser Leu Leu Thr Glu Val Glu Thr Pro Ile Arg Asn Glu Trp Gly Cys
1               5                   10                  15

Arg Cys Asn Asp Ser Ser Asp Pro
            20

<210> SEQ ID NO 11
<211> LENGTH: 130
<212> TYPE: PRT
<213> ORGANISM: Salmonella enterica

<400> SEQUENCE: 11

Ala Ala Ala Ser Leu Leu Thr Glu Val Glu Thr Pro Ile Arg Asn Glu
1               5                   10                  15

Trp Gly Ser Arg Ser Asn Asp Ser Ser Asp Pro Ala Ala Gly Thr Ser
            20                  25                  30

Ala Ala Ala Ser Leu Leu Thr Glu Val Glu Thr Pro Ile Arg Asn Glu
        35                  40                  45

Trp Gly Ser Arg Ser Asn Asp Ser Ser Asp Pro Ala Ala Ala Leu Gln
    50                  55                  60

Ala Ala Ala Ser Leu Leu Thr Glu Val Glu Thr Pro Ile Arg Asn Glu
65                  70                  75                  80

Trp Gly Ser Arg Ser Asn Asp Ser Ser Asp Pro Ala Ala Ala Ala Cys
                85                  90                  95

Ala Ala Ala Ser Leu Leu Thr Glu Val Glu Thr Pro Ile Arg Asn Glu
            100                 105                 110

Trp Gly Ser Arg Ser Asn Asp Ser Ser Asp Pro Ala Ala Ala Ala Cys
        115                 120                 125

Lys Leu
    130

<210> SEQ ID NO 12
<211> LENGTH: 495
<212> TYPE: PRT
<213> ORGANISM: Salmonella typhimurium

<400> SEQUENCE: 12

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45
```

```
Ala Ile Ala Asn Arg Phe Thr Ala Asn Ile Lys Gly Leu Thr Gln Ala
 50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ala
                 85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
            115                 120                 125

Gln Thr Gln Phe Asn Gly Val Lys Val Leu Ala Gln Asp Asn Thr Leu
130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
450                 455                 460

Asn Met Ser Arg Ala Gln Ile Leu Gln Gln Ala Gly Thr Ser Val Leu
```

```
            465                 470                 475                 480
Ala Gln Ala Asn Gln Val Pro Gln Asn Val Leu Ser Leu Leu Arg
                    485                 490                 495

<210> SEQ ID NO 13
<211> LENGTH: 506
<212> TYPE: PRT
<213> ORGANISM: Salmonella typhimurium

<400> SEQUENCE: 13

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val Gln
                165                 170                 175

Lys Ala Tyr Asp Val Lys Asp Thr Ala Val Thr Thr Lys Ala Tyr Ala
            180                 185                 190

Asn Asn Gly Thr Thr Leu Asp Val Ser Gly Leu Asp Asp Ala Ala Ile
        195                 200                 205

Lys Ala Ala Thr Gly Gly Thr Asn Gly Thr Ala Ser Val Thr Gly Gly
    210                 215                 220

Ala Val Lys Phe Asp Ala Asp Asn Asn Lys Tyr Phe Val Thr Ile Gly
225                 230                 235                 240

Gly Phe Thr Gly Ala Asp Ala Ala Lys Asn Gly Asp Tyr Glu Val Asn
                245                 250                 255

Val Ala Thr Asp Gly Thr Val Thr Leu Ala Ala Gly Ala Thr Lys Thr
            260                 265                 270

Thr Met Pro Ala Gly Ala Thr Thr Lys Thr Glu Val Gln Glu Leu Lys
        275                 280                 285

Asp Thr Pro Ala Val Val Ser Ala Asp Ala Lys Asn Ala Leu Ile Ala
    290                 295                 300

Gly Gly Val Asp Ala Thr Asp Ala Asn Gly Ala Glu Leu Val Lys Met
305                 310                 315                 320

Ser Tyr Thr Asp Lys Asn Gly Lys Thr Ile Glu Gly Gly Tyr Ala Leu
                325                 330                 335

Lys Ala Gly Asp Lys Tyr Tyr Ala Ala Asp Tyr Asp Glu Ala Thr Gly
            340                 345                 350
```

Ala Ile Lys Ala Lys Thr Thr Ser Tyr Thr Ala Ala Asp Gly Thr Thr
            355                 360                 365

Lys Thr Ala Ala Asn Gln Leu Gly Gly Val Asp Gly Lys Thr Glu Val
    370                 375                 380

Val Thr Ile Asp Gly Lys Thr Tyr Asn Ala Ser Lys Ala Ala Gly His
385                 390                 395                 400

Asp Phe Lys Ala Gln Pro Glu Leu Ala Glu Ala Ala Lys Thr Thr
                405                 410                 415

Glu Asn Pro Leu Gln Lys Ile Asp Ala Ala Leu Ala Gln Val Asp Ala
                420                 425                 430

Leu Arg Ser Asp Leu Gly Ala Val Gln Asn Arg Phe Asn Ser Ala Ile
            435                 440                 445

Thr Asn Leu Gly Asn Thr Val Asn Asn Leu Ser Glu Ala Arg Ser Arg
    450                 455                 460

Ile Glu Asp Ser Asp Tyr Ala Thr Glu Val Ser Asn Met Ser Arg Ala
465                 470                 475                 480

Gln Ile Leu Gln Gln Ala Gly Thr Ser Val Leu Ala Gln Ala Asn Gln
                485                 490                 495

Val Pro Gln Asn Val Leu Ser Leu Leu Arg
            500                 505

<210> SEQ ID NO 14
<211> LENGTH: 398
<212> TYPE: PRT
<213> ORGANISM: Salmonella typhimurium

<400> SEQUENCE: 14

Phe Thr Ala Asn Ile Lys Gly Leu Thr Gln Ala Ser Arg Asn Ala Asn
1               5                   10                  15

Asp Gly Ile Ser Ile Ala Gln Thr Thr Glu Gly Ala Leu Asn Glu Ile
            20                  25                  30

Asn Asn Asn Leu Gln Arg Val Arg Glu Leu Ala Val Gln Ser Ala Asn
        35                  40                  45

Ser Thr Asn Ser Gln Ser Asp Leu Asp Ser Ile Gln Ala Glu Ile Thr
    50                  55                  60

Gln Arg Leu Asn Glu Ile Asp Arg Val Ser Gly Gln Thr Gln Phe Asn
65              70                  75                  80

Gly Val Lys Val Leu Ala Gln Asp Asn Thr Leu Thr Ile Gln Val Gly
                85                  90                  95

Ala Asn Asp Gly Glu Thr Ile Asp Ile Asp Leu Lys Gln Ile Asn Ser
            100                 105                 110

Gln Thr Leu Gly Leu Asp Thr Leu Asn Val Gln Gln Lys Tyr Lys Val
        115                 120                 125

Ser Asp Thr Ala Ala Thr Val Thr Gly Tyr Ala Asp Thr Thr Ile Ala
    130                 135                 140

Leu Asp Asn Ser Thr Phe Lys Ala Ser Ala Thr Gly Leu Gly Gly Thr
145                 150                 155                 160

Asp Gln Lys Ile Asp Gly Asp Leu Lys Phe Asp Asp Thr Thr Gly Lys
                165                 170                 175

Tyr Tyr Ala Lys Val Thr Val Thr Gly Gly Thr Gly Lys Asp Gly Tyr
            180                 185                 190

Tyr Glu Val Ser Val Asp Lys Thr Asn Gly Glu Val Thr Leu Ala Gly
        195                 200                 205

Gly Ala Thr Ser Pro Leu Thr Gly Gly Leu Pro Ala Thr Ala Thr Glu
    210                 215                 220

```
Asp Val Lys Asn Val Gln Val Asn Ala Asp Leu Thr Glu Ala Lys
225                 230                 235                 240

Ala Ala Leu Thr Ala Ala Gly Val Thr Gly Thr Ala Ser Val Val Lys
            245                 250                 255

Met Ser Tyr Thr Asp Asn Asn Gly Lys Thr Ile Asp Gly Gly Leu Ala
        260                 265                 270

Val Lys Val Gly Asp Asp Tyr Tyr Ser Ala Thr Gln Asn Lys Asp Gly
    275                 280                 285

Ser Ile Ser Ile Asn Thr Thr Lys Tyr Thr Ala Asp Asp Gly Thr Ser
290                 295                 300

Lys Thr Ala Leu Asn Lys Leu Gly Gly Ala Asp Gly Lys Thr Glu Val
305                 310                 315                 320

Val Ser Ile Gly Gly Lys Thr Tyr Ala Ala Ser Lys Ala Glu Gly His
                325                 330                 335

Asn Phe Lys Ala Gln Pro Asp Leu Ala Glu Ala Ala Thr Thr Thr
            340                 345                 350

Glu Asn Pro Leu Gln Lys Ile Asp Ala Ala Leu Ala Gln Val Asp Thr
                355                 360                 365

Leu Arg Ser Asp Leu Ala Ala Val Gln Asn Arg Phe Asn Ser Ala Ile
370                 375                 380

Thr Asn Leu Gly Asn Thr Val Asn Asn Leu Thr Ser Ala Arg
385                 390                 395

<210> SEQ ID NO 15
<211> LENGTH: 290
<212> TYPE: PRT
<213> ORGANISM: Artificial Sequence
<220> FEATURE:
<223> OTHER INFORMATION: flagellin fusion protein

<400> SEQUENCE: 15

Met Ala Leu Thr Val Asn Thr Asn Ile Ala Ser Leu Asn Thr Gln Arg
1               5                   10                  15

Asn Leu Asn Asn Ser Ser Ala Ser Leu Asn Thr Ser Leu Gln Arg Leu
            20                  25                  30

Ser Thr Gly Ser Arg Ile Asn Ser Ala Lys Asp Asp Ala Ala Gly Leu
        35                  40                  45

Gln Ile Ala Asn Arg Leu Thr Ser Gln Val Asn Gly Leu Asn Val Ala
    50                  55                  60

Thr Lys Asn Ala Asn Asp Gly Ile Ser Leu Ala Gln Thr Ala Glu Gly
65                  70                  75                  80

Ala Leu Gln Gln Ser Thr Asn Ile Leu Gln Arg Met Arg Asp Leu Ser
                85                  90                  95

Leu Gln Ser Ala Asn Gly Ser Asn Ser Asp Ser Glu Arg Thr Ala Leu
            100                 105                 110

Asn Gly Glu Val Lys Gln Leu Gln Lys Glu Leu Asp Arg Ile Ser Asn
        115                 120                 125

Thr Thr Thr Phe Gly Gly Arg Lys Leu Leu Asp Gly Ser Phe Gly Val
    130                 135                 140

Ala Ser Phe Gln Val Gly Ser Ala Ala Asn Glu Ile Ile Ser Val Gly
145                 150                 155                 160

Ile Gly Gly Gly Lys Leu Met Ile Lys Leu Lys Phe Gly Val Phe Phe
                165                 170                 175

Thr Val Leu Leu Ser Ser Ala Tyr Ala His Gly Thr Pro Gln Asn Ile
            180                 185                 190
```

-continued

```
Thr Asp Leu Cys Ala Glu Tyr His Asn Thr Gln Ile His Thr Leu Asn
        195                 200                 205

Asp Lys Ile Phe Ser Tyr Thr Glu Ser Leu Ala Gly Lys Arg Glu Met
    210                 215                 220

Ala Ile Ile Thr Phe Lys Asn Gly Ala Thr Phe Gln Val Glu Val Pro
225                 230                 235                 240

Gly Ser Gln His Ile Asp Ser Gln Lys Lys Ala Ile Glu Arg Met Lys
                245                 250                 255

Asp Thr Leu Arg Ile Ala Tyr Leu Thr Glu Ala Lys Val Glu Lys Leu
            260                 265                 270

Cys Val Trp Asn Asn Lys Thr Pro His Ala Ile Ala Ala Ile Ser Met
        275                 280                 285

Ala Asn
    290

<210> SEQ ID NO 16
<211> LENGTH: 39
<212> TYPE: PRT
<213> ORGANISM: Artificial Sequence
<220> FEATURE:
<223> OTHER INFORMATION: polypeptide fragments of flagellin

<400> SEQUENCE: 16

Gly Ala Leu Asn Glu Ile Asn Asn Asn Leu Gln Arg Val Arg Glu Leu
1               5                   10                  15

Ala Val Gln Ser Ala Asn Ser Thr Asn Ser Gln Ser Asp Leu Asp Ser
                20                  25                  30

Ile Gln Ala Glu Ile Thr Gln
            35

<210> SEQ ID NO 17
<211> LENGTH: 44
<212> TYPE: PRT
<213> ORGANISM: Artificial Sequence
<220> FEATURE:
<223> OTHER INFORMATION: Polypeptide fragments of flagellin

<400> SEQUENCE: 17

Thr Gln Phe Ser Gly Val Lys Val Leu Ala Gln Asp Asn Thr Leu Thr
1               5                   10                  15

Ile Gln Val Gly Ala Asn Asp Gly Glu Thr Ile Asp Ile Asp Leu Lys
                20                  25                  30

Gln Ile Asn Ser Gln Thr Leu Gly Leu Asp Thr Leu
            35                  40

<210> SEQ ID NO 18
<211> LENGTH: 50
<212> TYPE: PRT
<213> ORGANISM: Artificial Sequence
<220> FEATURE:
<223> OTHER INFORMATION: Polypeptide fragments of flagellin

<400> SEQUENCE: 18

Glu Gly Ala Leu Asn Glu Ile Asn Asn Asn Leu Gln Arg Val Arg Glu
1               5                   10                  15

Leu Ala Val Gln Ser Ala Asn Ser Thr Asn Ser Gln Ser Asp Leu Asp
                20                  25                  30

Ser Ile Gln Ala Glu Ile Thr Gln Arg Leu Asn Glu Ile Asp Arg Val
            35                  40                  45
```

Asn Gly
    50

<210> SEQ ID NO 19
<211> LENGTH: 98
<212> TYPE: PRT
<213> ORGANISM: Artificial Sequence
<220> FEATURE:
<223> OTHER INFORMATION: Polypeptide fragments of flagellin

<400> SEQUENCE: 19

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Phe Thr Ala Asn Ile Lys Gly Leu Thr Gln Ala Ser
    50                  55                  60

Arg Asn Ala Asn Asp Gly Ile Ser Ile Ala Gln Thr Thr Glu Gly Ala
65                  70                  75                  80

Leu Asn Glu Ile Asn Asn Asn Leu Gln Arg Val Arg Glu Leu Ala Val
                85                  90                  95

Gln Ser

<210> SEQ ID NO 20
<211> LENGTH: 32
<212> TYPE: PRT
<213> ORGANISM: Artificial Sequence
<220> FEATURE:
<223> OTHER INFORMATION: Polypeptide fragments of flagellin

<400> SEQUENCE: 20

Leu Gln Lys Ile Asp Ala Ala Leu Ala Gln Val Asp Thr Leu Arg Ser
1               5                   10                  15

Asp Leu Gly Ala Val Gln Asn Arg Phe Asn Ser Ala Ile Thr Asn Leu
            20                  25                  30

<210> SEQ ID NO 21
<211> LENGTH: 29
<212> TYPE: PRT
<213> ORGANISM: Artificial Sequence
<220> FEATURE:
<223> OTHER INFORMATION: Polypeptide fragments of flagellin

<400> SEQUENCE: 21

Thr Leu Arg Ser Asp Leu Gly Ala Val Gln Asn Arg Phe Asn Ser Ala
1               5                   10                  15

Ile Thr Asn Leu Gly Asn Thr Val Asn Asn Leu Ser Ser
            20                  25

<210> SEQ ID NO 22
<211> LENGTH: 51
<212> TYPE: PRT
<213> ORGANISM: Artificial Sequence
<220> FEATURE:
<223> OTHER INFORMATION: Polypeptide fragments of flagellin

<400> SEQUENCE: 22

Glu Gln Ala Ala Lys Thr Thr Glu Asn Pro Leu Gln Lys Ile Asp Ala
1               5                   10                  15

Ala Leu Ala Gln Val Asp Thr Leu Arg Ser Asp Leu Gly Ala Val Gln

```
                    20                  25                  30

Asn Arg Phe Asn Ser Ala Ile Thr Asn Leu Gly Asn Thr Val Asn Asn
                35                  40                  45

Leu Ser Ser
        50

<210> SEQ ID NO 23
<211> LENGTH: 984
<212> TYPE: PRT
<213> ORGANISM: Artificial Sequence
<220> FEATURE:
<223> OTHER INFORMATION: CBLC502

<400> SEQUENCE: 23

Met Glu Thr Ala Arg Gly Gly Leu Tyr Ser Glu Arg His Ile Ser His
1               5                   10                  15

Ile Ser His Ile Ser His Ile Ser His Ile Ser His Ile Ser Gly Leu
                20                  25                  30

Tyr Met Glu Thr Ala Leu Ala Ser Glu Arg Met Glu Thr Thr His Arg
            35                  40                  45

Gly Leu Tyr Gly Leu Asn Gly Leu Asn Met Glu Thr Gly Leu Tyr Ala
        50                  55                  60

Arg Gly Ala Ser Pro Cys Thr Thr Thr Tyr Arg Ala Ser Pro Ala Ser
65                  70                  75                  80

Pro Ala Ser Pro Ala Ser Pro Leu Tyr Ser Ala Ser Pro Cys Cys Gly
                85                  90                  95

Met Glu Thr Ala Leu Ala Gly Leu Asn Val Ala Leu Ile Leu Glu Ala
            100                 105                 110

Ser Asn Thr His Arg Ala Ser Asn Ser Glu Arg Cys Thr Thr Ser Glu
        115                 120                 125

Arg Cys Thr Thr Cys Thr Thr Thr His Arg Gly Leu Asn Ala Ser Asn
130                 135                 140

Ala Ser Asn Cys Thr Thr Ala Ser Asn Leu Tyr Ser Ser Glu Arg Gly
145                 150                 155                 160

Leu Asn Ser Glu Arg Ser Glu Arg Cys Thr Thr Ser Glu Arg Ser Glu
                165                 170                 175

Arg Ala Leu Ala Ile Leu Glu Gly Ala Gly Ala Arg Gly Cys Thr Thr
            180                 185                 190

Ser Glu Arg Ser Glu Arg Gly Leu Tyr Cys Thr Thr Ala Arg Gly Ile
        195                 200                 205

Leu Glu Ala Ser Asn Ser Glu Arg Ala Leu Ala Leu Tyr Ser Ala Ser
    210                 215                 220

Pro Ala Ser Pro Ala Leu Ala Ala Leu Ala Gly Leu Tyr Gly Leu Asn
225                 230                 235                 240

Ala Leu Ala Ile Leu Glu Ala Leu Ala Ala Ser Asn Ala Arg Gly Pro
                245                 250                 255

His Glu Thr His Arg Ser Glu Arg Ala Ser Asn Ile Leu Glu Leu Tyr
            260                 265                 270

Ser Gly Leu Tyr Cys Thr Thr Thr His Arg Gly Leu Asn Ala Leu Ala
        275                 280                 285

Ser Glu Arg Ala Arg Gly Ala Ser Asn Ala Leu Ala Ala Ser Asn Ala
    290                 295                 300

Ser Pro Gly Leu Tyr Ile Leu Glu Ser Glu Arg Ile Leu Glu Ala Leu
305                 310                 315                 320

Ala Gly Leu Asn Thr His Arg Thr His Arg Gly Ala Gly Gly Leu Tyr
```

-continued

```
                325                 330                 335
Ala Leu Ala Cys Thr Thr Ala Ser Asn Gly Ala Gly Ile Leu Glu Ala
                340                 345                 350
Ser Asn Ala Ser Asn Ala Ser Asn Cys Thr Thr Gly Leu Asn Ala Arg
                355                 360                 365
Gly Val Ala Leu Ala Arg Gly Ala Gly Cys Thr Thr Ser Glu Arg
370                 375                 380
Val Ala Leu Gly Leu Asn Ala Leu Ala Thr His Arg Ala Ser Asn Gly
385                 390                 395                 400
Leu Tyr Thr His Arg Ala Ser Asn Ser Glu Arg Ala Ser Pro Ser Glu
                405                 410                 415
Arg Ala Ser Pro Cys Thr Thr Leu Tyr Ser Ser Glu Arg Ile Leu Glu
                420                 425                 430
Gly Leu Asn Ala Ser Pro Gly Ala Gly Ile Leu Glu Gly Leu Asn Gly
                435                 440                 445
Leu Asn Ala Arg Gly Cys Thr Thr Gly Ala Gly Gly Ala Gly Ile Leu
                450                 455                 460
Glu Ala Ser Pro Ala Arg Gly Val Ala Leu Ser Glu Arg Ala Ser Asn
465                 470                 475                 480
Gly Leu Asn Thr His Arg Gly Leu Asn Pro His Glu Ala Ser Asn Gly
                485                 490                 495
Leu Tyr Val Ala Leu Leu Tyr Ser Val Ala Leu Cys Thr Thr Ser Glu
                500                 505                 510
Arg Gly Leu Asn Ala Ser Pro Ala Ser Asn Gly Leu Asn Met Glu Thr
                515                 520                 525
Leu Tyr Ser Ile Leu Glu Gly Leu Asn Val Ala Leu Gly Leu Tyr Ala
                530                 535                 540
Leu Ala Ala Ser Asn Ala Ser Pro Gly Leu Tyr Gly Ala Gly Thr His
545                 550                 555                 560
Arg Ile Leu Glu Thr His Arg Ile Leu Glu Ala Ser Pro Cys Thr Thr
                565                 570                 575
Gly Leu Asn Leu Tyr Ser Ile Leu Glu Ala Ser Pro Val Ala Leu Leu
                580                 585                 590
Tyr Ser Ser Glu Arg Cys Thr Thr Gly Leu Tyr Cys Thr Thr Ala Ser
                595                 600                 605
Pro Gly Leu Tyr Pro His Glu Ala Ser Asn Val Ala Leu Ala Ser Asn
                610                 615                 620
Ser Glu Arg Cys Cys Gly Gly Leu Tyr Ile Leu Glu Ser Glu Arg Gly
625                 630                 635                 640
Leu Tyr Gly Leu Tyr Gly Leu Tyr Gly Leu Tyr Gly Leu Tyr Ile Leu
                645                 650                 655
Glu Cys Thr Thr Ala Ser Pro Ser Glu Arg Met Glu Thr Gly Leu Tyr
                660                 665                 670
Thr His Arg Cys Thr Thr Ile Leu Glu Ala Ser Asn Gly Ala Gly Ala
                675                 680                 685
Ser Pro Ala Leu Ala Ala Leu Ala Ala Leu Ala Leu Ala Leu Ala Tyr
                690                 695                 700
Ser Leu Tyr Ser Ser Glu Arg Thr His Arg Ala Leu Ala Ala Ser Asn
705                 710                 715                 720
Cys Cys Gly Cys Thr Thr Ala Leu Ala Ser Glu Arg Ile Leu Glu Ala
                725                 730                 735
Ser Pro Ser Glu Arg Ala Leu Ala Cys Thr Thr Ser Glu Arg Leu Tyr
                740                 745                 750
```

Ser Val Ala Leu Ala Ser Pro Ala Leu Ala Val Ala Leu Ala Arg Gly
            755                 760                 765

Ser Glu Arg Ser Glu Arg Cys Thr Thr Gly Leu Tyr Ala Leu Ala Ile
770                 775                 780

Leu Glu Gly Leu Asn Ala Ser Asn Ala Arg Gly Pro His Glu Ala Ser
785                 790                 795                 800

Pro Ser Glu Arg Ala Leu Ala Ile Leu Glu Thr His Arg Ala Ser Asn
            805                 810                 815

Cys Thr Thr Gly Leu Tyr Ala Ser Asn Thr His Arg Val Ala Leu Thr
            820                 825                 830

His Arg Ala Ser Asn Cys Thr Thr Ala Ser Asn Ser Glu Arg Ala Leu
            835                 840                 845

Ala Ala Arg Gly Ser Glu Arg Ala Arg Gly Ile Leu Glu Gly Ala Gly
850 855 860

Ala Ser Pro Ala Leu Ala Ala Ser Pro Thr Tyr Arg Ala Leu Ala Thr
865 870 875 880

His Arg Gly Ala Gly Val Ala Leu Ser Glu Arg Ala Ser Asn Met Glu
885 890 895

Thr Ser Glu Arg Leu Tyr Ser Ala Leu Ala Gly Leu Asn Ile Leu Glu
900 905 910

Cys Thr Thr Gly Leu Asn Gly Leu Asn Ala Leu Ala Gly Leu Tyr Thr
915 920 925

His Arg Ser Glu Arg Val Ala Leu Cys Thr Thr Ala Leu Ala Gly Leu
930 935 940

Asn Ala Leu Ala Ala Ser Asn Gly Leu Asn Val Ala Leu Cys Cys Gly
945 950 955 960

Gly Leu Asn Ala Ser Asn Val Ala Leu Cys Thr Thr Ser Glu Arg Cys
965 970 975

Thr Thr Cys Thr Thr Ala Arg Gly
980

<210> SEQ ID NO 24
<211> LENGTH: 27
<212> TYPE: PRT
<213> ORGANISM: Influenza A virus

<400> SEQUENCE: 24

Asp Trp Ile Leu Trp Ile Ser Phe Ala Ile Ser Cys Phe Leu Leu Cys
1 5 10 15

Val Ala Leu Leu Gly Phe Ile Met Trp Ala Cys
20 25

<210> SEQ ID NO 25
<211> LENGTH: 11
<212> TYPE: PRT
<213> ORGANISM: Influenza A virus

<400> SEQUENCE: 25

Gln Lys Gly Asn Ile Arg Cys Asn Ile Cys Ile
1 5 10

<210> SEQ ID NO 26
<211> LENGTH: 29
<212> TYPE: PRT
<213> ORGANISM: Influenza A virus

<400> SEQUENCE: 26

Met Lys Phe Leu Val Asn Val Ala Leu Val Phe Met Val Val Tyr Ile
1               5                   10                  15

Ser Tyr Ile Tyr Ala Asp Pro Ile Asn Met Thr Gly Ser
            20                  25

<210> SEQ ID NO 27
<211> LENGTH: 1095
<212> TYPE: DNA
<213> ORGANISM: Artificial Sequence
<220> FEATURE:
<223> OTHER INFORMATION: truncated

<400> SEQUENCE: 27

```
atgaaattct tagtcaacgt tgcccttgtt tttatggtcg tgtacatttc ttacatctat      60
gcggacccga tcaacatgac cggatccatg gcacaagtca ttaatacaaa cagcctgtcg     120
ctgttgaccc agaataacct gaacaaatcc cagtccgctc tgggcaccgc tatcgagcgt     180
ctgtcttccg gtctgcgtat caacagcgcg aaagacgatg cggcaggtca ggcgattgct     240
aaccgtttta ccgcgaacat caaaggtctg actcaggctt cccgtaacgc taacgacggt     300
atctccattg cgcagaccac tgaaggcgcg ctgaacgaaa tcaacaacaa cctgcagcgt     360
gtgcgtgaac tggcggttca gtctgctaac agcaccaact cccagtctga cctcgactcc     420
atccaggctg aaatcaccca gcgcctgaac gaaatcgacc gtgtatccgg ccagactcag     480
ttcaacggcg tgaaagtcct ggcgcaggac aacaccctga ccatccaggt tggtgccaac     540
gacggtgaaa ctatcgatat cgatctgaag cagatcaact ctcagaccct gggtctggat     600
acgctgaatg tgggcgcgcc ggtctacccg tatgacgtgc cggactacgc gtcgccatgg     660
acaaccaccg aaaacccgct gcagaaaatt gatgctgctt ggcacaggt tgacacgtta      720
cgttctgacc tgggtgcggt acagaaccgt ttcaactccg ctattaccaa cctgggcaac     780
accgtaaaca acctgacttc tgcccgtagc cgtatcgaag attccgacta cgcgaccgaa     840
gtttccaaca tgtctcgcgc gcagattctg cagcaggccg taccctccgt tctggcgcag     900
gcgaaccagg ttccgcaaaa cgtcctctct ttactgcgtg aattcggagt gaaattggaa     960
tcaatgggga tctatcagat tctggcgatc tactcaactg tcgccagttc actggtgctt    1020
ttggtctccc tggggcaat cagtttctgg atgtgttcta atggatcttt gcagtgcaga     1080
atatgcatct gataa                                                    1095
```

<210> SEQ ID NO 28
<211> LENGTH: 363
<212> TYPE: PRT
<213> ORGANISM: Artificial Sequence
<220> FEATURE:
<223> OTHER INFORMATION: truncated

<400> SEQUENCE: 28

Met Lys Phe Leu Val Asn Val Ala Leu Val Phe Met Val Val Tyr Ile
1               5                   10                  15

Ser Tyr Ile Tyr Ala Asp Pro Ile Asn Met Thr Gly Ser Met Ala Gln
            20                  25                  30

Val Ile Asn Thr Asn Ser Leu Ser Leu Leu Thr Gln Asn Asn Leu Asn
        35                  40                  45

Lys Ser Gln Ser Ala Leu Gly Thr Ala Ile Glu Arg Leu Ser Ser Gly
    50                  55                  60

Leu Arg Ile Asn Ser Ala Lys Asp Asp Ala Ala Gly Gln Ala Ile Ala
65                  70                  75                  80

Asn Arg Phe Thr Ala Asn Ile Lys Gly Leu Thr Gln Ala Ser Arg Asn
            85                  90                  95

Ala Asn Asp Gly Ile Ser Ile Ala Gln Thr Thr Glu Gly Ala Leu Asn
            100                 105                 110

Glu Ile Asn Asn Asn Leu Gln Arg Val Arg Glu Leu Ala Val Gln Ser
            115                 120                 125

Ala Asn Ser Thr Asn Ser Gln Ser Asp Leu Asp Ser Ile Gln Ala Glu
            130                 135                 140

Ile Thr Gln Arg Leu Asn Glu Ile Asp Arg Val Ser Gly Gln Thr Gln
145                 150                 155                 160

Phe Asn Gly Val Lys Val Leu Ala Gln Asp Asn Thr Leu Thr Ile Gln
                165                 170                 175

Val Gly Ala Asn Asp Gly Glu Thr Ile Asp Ile Asp Leu Lys Gln Ile
            180                 185                 190

Asn Ser Gln Thr Leu Gly Leu Asp Thr Leu Asn Val Gly Ala Pro Val
            195                 200                 205

Tyr Pro Tyr Asp Val Pro Asp Tyr Ala Ser Pro Trp Thr Thr Thr Glu
            210                 215                 220

Asn Pro Leu Gln Lys Ile Asp Ala Ala Leu Ala Gln Val Asp Thr Leu
225                 230                 235                 240

Arg Ser Asp Leu Gly Ala Val Gln Asn Arg Phe Asn Ser Ala Ile Thr
                245                 250                 255

Asn Leu Gly Asn Thr Val Asn Asn Leu Thr Ser Ala Arg Ser Arg Ile
            260                 265                 270

Glu Asp Ser Asp Tyr Ala Thr Glu Val Ser Asn Met Ser Arg Ala Gln
            275                 280                 285

Ile Leu Gln Gln Ala Gly Thr Ser Val Leu Ala Gln Ala Asn Gln Val
            290                 295                 300

Pro Gln Asn Val Leu Ser Leu Leu Arg Glu Phe Gly Val Lys Leu Glu
305                 310                 315                 320

Ser Met Gly Ile Tyr Gln Ile Leu Ala Ile Tyr Ser Thr Val Ala Ser
                325                 330                 335

Ser Leu Val Leu Leu Val Ser Leu Gly Ala Ile Ser Phe Trp Met Cys
            340                 345                 350

Ser Asn Gly Ser Leu Gln Cys Arg Ile Cys Ile
            355                 360

<210> SEQ ID NO 29
<211> LENGTH: 23
<212> TYPE: PRT
<213> ORGANISM: Salmonella typhimurium

<400> SEQUENCE: 29

Ser Leu Leu Thr Glu Val Glu Thr Pro Ile Arg Asn Glu Trp Gly Ser
1               5                   10                  15

Arg Ser Asn Asp Ser Ser Asp
            20

<210> SEQ ID NO 30
<211> LENGTH: 22
<212> TYPE: PRT
<213> ORGANISM: Salmonella typhimurium

<400> SEQUENCE: 30

Ser Leu Leu Thr Glu Val Glu Thr Pro Ile Arg Asn Glu Trp Gly Ser
1               5                   10                  15

Arg Ser Asn Asp Ser Ser
            20

<210> SEQ ID NO 31
<211> LENGTH: 21
<212> TYPE: PRT
<213> ORGANISM: Salmonella typhimurium

<400> SEQUENCE: 31

Ser Leu Leu Thr Glu Val Glu Thr Pro Ile Arg Asn Glu Trp Gly Ser
1               5                   10                  15

Arg Ser Asn Asp Ser
            20

<210> SEQ ID NO 32
<211> LENGTH: 20
<212> TYPE: PRT
<213> ORGANISM: Salmonella typhimurium

<400> SEQUENCE: 32

Ser Leu Leu Thr Glu Val Glu Thr Pro Ile Arg Asn Glu Trp Gly Ser
1               5                   10                  15

Arg Ser Asn Asp
            20

<210> SEQ ID NO 33
<211> LENGTH: 19
<212> TYPE: PRT
<213> ORGANISM: Salmonella typhimurium

<400> SEQUENCE: 33

Ser Leu Leu Thr Glu Val Glu Thr Pro Ile Arg Asn Glu Trp Gly Ser
1               5                   10                  15

Arg Ser Asn

<210> SEQ ID NO 34
<211> LENGTH: 18
<212> TYPE: PRT
<213> ORGANISM: Salmonella typhimurium

<400> SEQUENCE: 34

Ser Leu Leu Thr Glu Val Glu Thr Pro Ile Arg Asn Glu Trp Gly Ser
1               5                   10                  15

Arg Ser

<210> SEQ ID NO 35
<211> LENGTH: 17
<212> TYPE: PRT
<213> ORGANISM: Salmonella typhimurium

<400> SEQUENCE: 35

Ser Leu Leu Thr Glu Val Glu Thr Pro Ile Arg Asn Glu Trp Gly Ser
1               5                   10                  15

Arg

<210> SEQ ID NO 36
<211> LENGTH: 16
<212> TYPE: PRT
<213> ORGANISM: Salmonella typhimurium

<400> SEQUENCE: 36

Ser Leu Leu Thr Glu Val Glu Thr Pro Ile Arg Asn Glu Trp Gly Ser

```
<210> SEQ ID NO 37
<211> LENGTH: 15
<212> TYPE: PRT
<213> ORGANISM: Salmonella typhimurium

<400> SEQUENCE: 37

Ser Leu Leu Thr Glu Val Glu Thr Pro Ile Arg Asn Glu Trp Gly
1               5                   10                  15

<210> SEQ ID NO 38
<211> LENGTH: 14
<212> TYPE: PRT
<213> ORGANISM: Salmonella typhimurium

<400> SEQUENCE: 38

Ser Leu Leu Thr Glu Val Glu Thr Pro Ile Arg Asn Glu Trp
1               5                   10

<210> SEQ ID NO 39
<211> LENGTH: 13
<212> TYPE: PRT
<213> ORGANISM: Salmonella typhimurium

<400> SEQUENCE: 39

Ser Leu Leu Thr Glu Val Glu Thr Pro Ile Arg Asn Glu
1               5                   10

<210> SEQ ID NO 40
<211> LENGTH: 12
<212> TYPE: PRT
<213> ORGANISM: Salmonella typhimurium

<400> SEQUENCE: 40

Ser Leu Leu Thr Glu Val Glu Thr Pro Ile Arg Asn
1               5                   10

<210> SEQ ID NO 41
<211> LENGTH: 11
<212> TYPE: PRT
<213> ORGANISM: Salmonella typhimurium

<400> SEQUENCE: 41

Ser Leu Leu Thr Glu Val Glu Thr Pro Ile Arg
1               5                   10

<210> SEQ ID NO 42
<211> LENGTH: 10
<212> TYPE: PRT
<213> ORGANISM: Salmonella typhimurium

<400> SEQUENCE: 42

Ser Leu Leu Thr Glu Val Glu Thr Pro Ile
1               5                   10

<210> SEQ ID NO 43
<211> LENGTH: 9
<212> TYPE: PRT
<213> ORGANISM: Salmonella typhimurium

<400> SEQUENCE: 43

Ser Leu Leu Thr Glu Val Glu Thr Pro
1               5
```

```
<210> SEQ ID NO 44
<211> LENGTH: 8
<212> TYPE: PRT
<213> ORGANISM: Salmonella typhimurium

<400> SEQUENCE: 44

Ser Leu Leu Thr Glu Val Glu Thr
1               5

<210> SEQ ID NO 45
<211> LENGTH: 7
<212> TYPE: PRT
<213> ORGANISM: Salmonella typhimurium

<400> SEQUENCE: 45

Ser Leu Leu Thr Glu Val Glu
1               5

<210> SEQ ID NO 46
<211> LENGTH: 6
<212> TYPE: PRT
<213> ORGANISM: Salmonella typhimurium

<400> SEQUENCE: 46

Ser Leu Leu Thr Glu Val
1               5

<210> SEQ ID NO 47
<211> LENGTH: 5
<212> TYPE: PRT
<213> ORGANISM: Salmonella typhimurium

<400> SEQUENCE: 47

Ser Leu Leu Thr Glu
1               5

<210> SEQ ID NO 48
<211> LENGTH: 4
<212> TYPE: PRT
<213> ORGANISM: Salmonella typhimurium

<400> SEQUENCE: 48

Ser Leu Leu Thr
1

<210> SEQ ID NO 49
<211> LENGTH: 4
<212> TYPE: PRT
<213> ORGANISM: Salmonella typhimurium

<400> SEQUENCE: 49

Leu Leu Thr Glu
1

<210> SEQ ID NO 50
<211> LENGTH: 5
<212> TYPE: PRT
<213> ORGANISM: Salmonella typhimurium

<400> SEQUENCE: 50

Leu Leu Thr Glu Val
1               5

<210> SEQ ID NO 51
```

```
<211> LENGTH: 6
<212> TYPE: PRT
<213> ORGANISM: Salmonella typhimurium

<400> SEQUENCE: 51

Leu Leu Thr Glu Val Glu
1               5

<210> SEQ ID NO 52
<211> LENGTH: 7
<212> TYPE: PRT
<213> ORGANISM: Salmonella typhimurium

<400> SEQUENCE: 52

Leu Leu Thr Glu Val Glu Thr
1               5

<210> SEQ ID NO 53
<211> LENGTH: 8
<212> TYPE: PRT
<213> ORGANISM: Salmonella typhimurium

<400> SEQUENCE: 53

Leu Leu Thr Glu Val Glu Thr Pro
1               5

<210> SEQ ID NO 54
<211> LENGTH: 9
<212> TYPE: PRT
<213> ORGANISM: Salmonella typhimurium

<400> SEQUENCE: 54

Leu Leu Thr Glu Val Glu Thr Pro Ile
1               5

<210> SEQ ID NO 55
<211> LENGTH: 10
<212> TYPE: PRT
<213> ORGANISM: Salmonella typhimurium

<400> SEQUENCE: 55

Leu Leu Thr Glu Val Glu Thr Pro Ile Arg
1               5                   10

<210> SEQ ID NO 56
<211> LENGTH: 11
<212> TYPE: PRT
<213> ORGANISM: Salmonella typhimurium

<400> SEQUENCE: 56

Leu Leu Thr Glu Val Glu Thr Pro Ile Arg Asn
1               5                   10

<210> SEQ ID NO 57
<211> LENGTH: 4
<212> TYPE: PRT
<213> ORGANISM: Salmonella typhimurium

<400> SEQUENCE: 57

Leu Thr Glu Val
1

<210> SEQ ID NO 58
<211> LENGTH: 5
<212> TYPE: PRT
```

<213> ORGANISM: Salmonella typhimurium

<400> SEQUENCE: 58

Leu Thr Glu Val Glu
1               5

<210> SEQ ID NO 59
<211> LENGTH: 6
<212> TYPE: PRT
<213> ORGANISM: Salmonella typhimurium

<400> SEQUENCE: 59

Leu Thr Glu Val Glu Thr
1               5

<210> SEQ ID NO 60
<211> LENGTH: 7
<212> TYPE: PRT
<213> ORGANISM: Salmonella typhimurium

<400> SEQUENCE: 60

Leu Thr Glu Val Glu Thr Pro
1               5

<210> SEQ ID NO 61
<211> LENGTH: 8
<212> TYPE: PRT
<213> ORGANISM: Salmonella typhimurium

<400> SEQUENCE: 61

Leu Thr Glu Val Glu Thr Pro Ile
1               5

<210> SEQ ID NO 62
<211> LENGTH: 9
<212> TYPE: PRT
<213> ORGANISM: Salmonella typhimurium

<400> SEQUENCE: 62

Leu Thr Glu Val Glu Thr Pro Ile Arg
1               5

<210> SEQ ID NO 63
<211> LENGTH: 10
<212> TYPE: PRT
<213> ORGANISM: Salmonella typhimurium

<400> SEQUENCE: 63

Leu Thr Glu Val Glu Thr Pro Ile Arg Asn
1               5                   10

<210> SEQ ID NO 64
<211> LENGTH: 5
<212> TYPE: PRT
<213> ORGANISM: Salmonella typhimurium

<400> SEQUENCE: 64

Thr Glu Val Glu Val
1               5

<210> SEQ ID NO 65
<211> LENGTH: 5
<212> TYPE: PRT
<213> ORGANISM: Salmonella typhimurium

<400> SEQUENCE: 65

Thr Glu Val Glu Thr
1               5

<210> SEQ ID NO 66
<211> LENGTH: 6
<212> TYPE: PRT
<213> ORGANISM: Salmonella typhimurium

<400> SEQUENCE: 66

Thr Glu Val Glu Thr Pro
1               5

<210> SEQ ID NO 67
<211> LENGTH: 7
<212> TYPE: PRT
<213> ORGANISM: Salmonella typhimurium

<400> SEQUENCE: 67

Thr Glu Val Glu Thr Pro Ile
1               5

<210> SEQ ID NO 68
<211> LENGTH: 8
<212> TYPE: PRT
<213> ORGANISM: Salmonella typhimurium

<400> SEQUENCE: 68

Thr Glu Val Glu Thr Pro Ile Arg
1               5

<210> SEQ ID NO 69
<211> LENGTH: 9
<212> TYPE: PRT
<213> ORGANISM: Salmonella typhimurium

<400> SEQUENCE: 69

Thr Glu Val Glu Thr Pro Ile Arg Asn
1               5

<210> SEQ ID NO 70
<211> LENGTH: 4
<212> TYPE: PRT
<213> ORGANISM: Salmonella typhimurium

<400> SEQUENCE: 70

Glu Val Glu Thr
1

<210> SEQ ID NO 71
<211> LENGTH: 5
<212> TYPE: PRT
<213> ORGANISM: Salmonella typhimurium

<400> SEQUENCE: 71

Glu Val Glu Thr Pro
1               5

<210> SEQ ID NO 72
<211> LENGTH: 6
<212> TYPE: PRT
<213> ORGANISM: Salmonella typhimurium

<400> SEQUENCE: 72

Glu Val Glu Thr Pro Ile
1               5

<210> SEQ ID NO 73
<211> LENGTH: 7
<212> TYPE: PRT
<213> ORGANISM: Salmonella typhimurium

<400> SEQUENCE: 73

Glu Val Glu Thr Pro Ile Arg
1               5

<210> SEQ ID NO 74
<211> LENGTH: 8
<212> TYPE: PRT
<213> ORGANISM: Salmonella typhimurium

<400> SEQUENCE: 74

Glu Val Glu Thr Pro Ile Arg Asn
1               5

<210> SEQ ID NO 75
<211> LENGTH: 5
<212> TYPE: PRT
<213> ORGANISM: Salmonella typhimurium

<400> SEQUENCE: 75

Val Glu Thr Pro Ile
1               5

<210> SEQ ID NO 76
<211> LENGTH: 6
<212> TYPE: PRT
<213> ORGANISM: Salmonella typhimurium

<400> SEQUENCE: 76

Val Glu Thr Pro Ile Arg
1               5

<210> SEQ ID NO 77
<211> LENGTH: 7
<212> TYPE: PRT
<213> ORGANISM: Salmonella typhimurium

<400> SEQUENCE: 77

Val Glu Thr Pro Ile Arg Asn
1               5

<210> SEQ ID NO 78
<211> LENGTH: 4
<212> TYPE: PRT
<213> ORGANISM: Salmonella typhimurium

<400> SEQUENCE: 78

Glu Thr Pro Ile
1

<210> SEQ ID NO 79
<211> LENGTH: 5
<212> TYPE: PRT
<213> ORGANISM: Salmonella typhimurium

<400> SEQUENCE: 79

Glu Thr Pro Ile Arg
1               5

<210> SEQ ID NO 80
<211> LENGTH: 6
<212> TYPE: PRT
<213> ORGANISM: Salmonella typhimurium

<400> SEQUENCE: 80

Glu Thr Pro Ile Arg Asn
1               5

<210> SEQ ID NO 81
<211> LENGTH: 5
<212> TYPE: PRT
<213> ORGANISM: Salmonella typhimurium

<400> SEQUENCE: 81

Thr Pro Ile Arg Asn
1               5

<210> SEQ ID NO 82
<211> LENGTH: 35
<212> TYPE: DNA
<213> ORGANISM: Artificial Sequence
<220> FEATURE:
<223> OTHER INFORMATION: HEp-2 cells

<400> SEQUENCE: 82
aaagaattca ccatggagga gttgctaatc ctcaa                                35

<210> SEQ ID NO 83
<211> LENGTH: 33
<212> TYPE: DNA
<213> ORGANISM: Artificial Sequence
<220> FEATURE:
<223> OTHER INFORMATION: HEp-2 cells

<400> SEQUENCE: 83
ttactcgagt tagttactaa atgcaatatt att                                  33

<210> SEQ ID NO 84
<211> LENGTH: 34
<212> TYPE: DNA
<213> ORGANISM: Artificial Sequence
<220> FEATURE:
<223> OTHER INFORMATION: RSV-G Gene

<400> SEQUENCE: 84
aaagaattca ccatgtccaa aacaaggac caac                                  34

<210> SEQ ID NO 85
<211> LENGTH: 27
<212> TYPE: DNA
<213> ORGANISM: Artificial Sequence
<220> FEATURE:
<223> OTHER INFORMATION: RSV-G gene

<400> SEQUENCE: 85
ttactcgagt actggcgtgg tgtgttg                                         27

<210> SEQ ID NO 86
<211> LENGTH: 32
<212> TYPE: DNA
<213> ORGANISM: Artificial Sequence
<220> FEATURE:
<223> OTHER INFORMATION: influenza M1 gene

```
<400> SEQUENCE: 86
aaagaattca ccatgagtct tctaaccgag gt                                    32

<210> SEQ ID NO 87
<211> LENGTH: 30
<212> TYPE: DNA
<213> ORGANISM: Artificial Sequence
<220> FEATURE:
<223> OTHER INFORMATION: influenza M1 gene

<400> SEQUENCE: 87
ttactcgagt tactctagct ctatgttgac                                       30

<210> SEQ ID NO 88
<211> LENGTH: 298
<212> TYPE: PRT
<213> ORGANISM: Artificial Sequence
<220> FEATURE:
<223> OTHER INFORMATION: RSV G" protein

<400> SEQUENCE: 88
```

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

```
Pro Ser Ser Pro Pro Asn Thr Pro Arg Gln
    290                 295

<210> SEQ ID NO 89
<211> LENGTH: 17
<212> TYPE: PRT
<213> ORGANISM: Artificial Sequence
<220> FEATURE:
<223> OTHER INFORMATION: M2e peptide

<400> SEQUENCE: 89

Ser Leu Leu Thr Glu Val Glu Thr Pro Ile Arg Asn Glu Trp Gly Cys
1               5                   10                  15

Arg
```